(12) United States Patent
Tajima et al.

(10) Patent No.: US 10,660,584 B2
(45) Date of Patent: May 26, 2020

(54) MONITOR IMAGE DISPLAY METHOD FOR RADIATION-IRRADIATION DEVICE AND RADIATION-IRRADIATION DEVICE

(71) Applicant: FUJIFILM Corporation, Tokyo (JP)

(72) Inventors: Takashi Tajima, Kanagawa (JP); Haruyasu Nakatsugawa, Kanagawa (JP); Takeshi Ohkubo, Kanagawa (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 276 days.

(21) Appl. No.: 15/914,104

(22) Filed: Mar. 7, 2018

(65) Prior Publication Data

US 2018/0192970 A1 Jul. 12, 2018

Related U.S. Application Data

(63) Continuation of application No. PCT/JP2016/003918, filed on Aug. 29, 2016.

(30) Foreign Application Priority Data

Sep. 8, 2015 (JP) .................. 2015-176638

(51) Int. Cl.
*A61B 6/00* (2006.01)
*A61B 6/10* (2006.01)
*A61B 6/08* (2006.01)

(52) U.S. Cl.
CPC .................. *A61B 6/10* (2013.01); *A61B 6/08* (2013.01); *A61B 6/102* (2013.01); *A61B 6/4405* (2013.01); *A61B 6/461* (2013.01)

(58) Field of Classification Search
CPC ......... A61B 6/107; A61B 6/0492; A61B 6/08; A61B 6/542; A61B 2090/3937; A61B 2090/3966; A61B 2090/3979; A61B 6/465; A61B 6/508; A61B 6/467; G06F 3/0485
See application file for complete search history.

(56) References Cited

U.S. PATENT DOCUMENTS

2017/0215823 A1* 8/2017 Ivanov .................. A61B 90/37

FOREIGN PATENT DOCUMENTS

| JP | 2007-313252 A | 12/2007 |
| JP | 2009-183368 A | 8/2009 |
| JP | 2012-029889 A | 2/2012 |
| JP | 2014-073311 A | 4/2014 |
| JP | 2015-156896 A | 9/2015 |

(Continued)

OTHER PUBLICATIONS

Supplemental European Search Report dated Sep. 3, 2018, issued by the European Patent Office for EP 16 843 910.7.

(Continued)

*Primary Examiner* — Don K Wong
(74) *Attorney, Agent, or Firm* — Sughrue Mion, PLLC

(57) ABSTRACT

There are provided a radiation-irradiation device and a monitor image display method for the radiation-irradiation device that allow a device operator to confirm a situation on the front side in a traveling direction in a case in which the device operator makes a radiation-irradiation device holding a radiation source travel and also allow the operator to confirm a situation around a subject in a case in which the device operator takes a radiation image.

20 Claims, 16 Drawing Sheets

(56) References Cited

FOREIGN PATENT DOCUMENTS

WO 2015/073105 A1 5/2015

OTHER PUBLICATIONS

"X-ray equipment IPF-21", Toshiba Medical Supply Co., Ltd., [online], [Search on Jul. 30, 1999], Internet URL:http://www.toshiba-rvouyouhin.co.jp/tmeds/xrays/ipf21.html (3 pages total).
International Search Report for PCT/JP2016/003918, dated Dec. 27, 2016.
International Preliminary Report on Patentability issued from the International Bureau in counterpart International Application No. PCT/J P2016/003918, dated Mar. 13, 2018.
Written Opinion dated Dec. 27, 2016, issued by the International Bureau in counterpart Application No. PCT/JP2016/003918.

* cited by examiner

MONITOR IMAGE DISPLAY METHOD FOR RADIATION-IRRADIATION DEVICE AND RADIATION-IRRADIATION DEVICE

CROSS-REFERENCE TO RELATED APPLICATION

This application is a continuation application of International Application No. PCT/JP2016/003918, filed Aug. 29, 2016, the disclosure of which is incorporated herein by reference in its entirety. Further, this application claims priority from Japanese Patent Application No. 2015-176638 filed Sep. 8, 2015, the disclosure of which is incorporated herein by reference in its entirety.

BACKGROUND

1. Field of the Invention

The present invention relates to a radiation-irradiation device that irradiates a subject with radiation in a case in which the radiation image of the subject is to be acquired.

Further, the invention relates to a monitor image display method for the radiation-irradiation device.

2. Description of the Related Art

In the past, a portable radiation-irradiation device, on which only a minimum number of components for radiation irradiation, such as a radiation source and an electrical circuit, are mounted and which can be operated while being held with hands by an operator, has been proposed as disclosed in, for example, JP2012-029889A and "Toshiba Medical Supply Co., Ltd., X-ray equipment IPF-21, [online], [Search on Jul. 30, 1999], Internet URL:http://www.toshiba-iryouyouhin.co.jp/tmeds/xrays/ipf21.html". Since this kind of portable radiation-irradiation device is reduced in weight so that an operator can hold and operate the radiation-irradiation device with hands, the radiation-irradiation device is advantageous for the imaging of a subject in various directions.

A radiation detector (so-called "Flat Panel Detector"), which records a radiation image representing a subject by being irradiated with radiation transmitted through the subject, is generally used in a case in which the radiation image of the subject is to be taken by this kind of radiographic imaging apparatus. A cassette-type radiation detector having a structure in which an image detection unit and a control unit, such as a battery for drive and an electrical circuit relating to drive, are received in a housing is well known as the radiation detector. Further, in a case in which such a radiation detector is disposed at a position facing the radiation-irradiation device with a subject interposed therebetween and the radiation-irradiation device is driven in this state, the radiation detector is irradiated with radiation transmitted through the subject. Accordingly, a radiation image represented by the radiation transmitted through the subject is acquired.

The portable radiation-irradiation device can be held and operated with hands by an operator. However, a radiation-irradiation device, which includes a holding unit holding a radiation source unit including a radiation source, is proposed to prevent shaking and to prevent operator's hands or the like from being exposed to radiation. "Toshiba Medical Supply Co., Ltd., X-ray equipment IPF-21, [online], [Search on Jul. 30, 1999], Internet URL:http://www.toshiba-iryouyouhin.co.jp/tmeds/xrays/ipf21.html" also discloses an example of such a holding unit, and particularly, a holding unit that includes wheel parts provided at lower portions of holding legs and can travel.

The radiation-irradiation device including the holding unit basically includes: a leg unit that is adapted to be capable of traveling using wheels; a body unit that receives a control unit including a battery for the drive of a radiation source, an electrical circuit relating to the drive of the radiation source, and the like and is held on the leg unit; and an arm unit that is connected to the body unit. The radiation source unit is mounted on the distal end of the arm unit.

In a case in which the radiation-irradiation device, which is adapted to be capable of traveling as described above, is used to take a radiation image, the radiation-irradiation device is transported to an imaging site by a transport force of an operator (user) or power.

However, the collision or interference between the radiation-irradiation device and a transport path or obstacles, which are present near the transport path, should be naturally avoided during the transport of the radiation-irradiation device.

JP2007-313252A discloses a radiographic imaging apparatus for round visit that images a field of view on the front side in a traveling direction of the apparatus by a camera, and displays the taken image on a monitor (display device) for displaying a radiation image at the time of radiographic imaging. According to this apparatus, since an operator of the apparatus can grasp a situation on the front side in the transport direction of the apparatus by observing the image of the monitor, it is possible to prevent the apparatus from colliding or interfering with obstacles.

SUMMARY

Incidentally, it is also important to confirm the situation around a subject (object) at the time of taking of a radiation image. That is, if this situation can be confirmed, work relating to the taking of a radiation image, such as work for setting the position of the radiation source unit so that a radiation-irradiation field is matched with the radiation detector, is facilitated.

However, it is not possible to confirm the situation around a subject at the time of taking of a radiation image in the apparatus disclosed in JP2007-313252A.

The invention has been made in consideration of the circumstances, and an object of the invention is to provide a monitor image display method for a radiation-irradiation device that allows a device operator to confirm a situation on the front side in a traveling direction in a case in which the device operator makes a radiation-irradiation device holding a radiation source travel and also allow the operator to confirm a situation around a subject in a case in which the device operator takes a radiation image.

Further, an object of the invention is to provide a radiation-irradiation device that can perform the monitor image display method.

There is provided a monitor image display method for a radiation-irradiation device according to the invention that irradiates a radiation image recording medium with radiation to take a radiation image and is adapted to be capable of traveling. The radiation-irradiation device includes a radiation source that generates radiation, a radiation source holding unit that is capable of at least setting the radiation source to a direction in which the radiation source irradiates the radiation image recording medium with radiation at the time of radiation irradiation and setting the radiation source to a vertically downward direction, at least one optical camera that is capable of taking at least a front image showing a field of view on a front side in a traveling direction of the radiation-irradiation device and an irradiation-direction image showing a field of view in a radiation-irradiation direction at the time of radiation irradiation, and a monitor that displays the image taken by the optical camera. The monitor image display method includes displaying the irradiation-direction image on the monitor in a case in which the radiation source is set to a direction other than a downward direction, displaying the irradiation-direction image on the monitor in a case in which the radiation source is set to the downward direction and a first condition is satisfied, and displaying the front image on the monitor in a case in which the radiation source is set to the downward direction and a second condition different from the first condition is satisfied.

In the monitor image display method for a radiation-irradiation device according to the invention, it is preferable that, in a case in which the radiation source holding unit is to take a non-storage state where the radiation source holding unit is unfolded and a storage state, a condition in which the radiation source holding unit is in the non-storage state is set as the first condition and a condition in which the radiation source holding unit is in the storage state is set as the second condition.

Here, the "storage state" means a state in which a joint-like portion rotationally moving is folded or a telescopic portion is made to contract so as to be made relatively small and cannot be generally used for radiation irradiation in this state. Further, the "non-storage state" means a state in which a portion rotationally moving is slightly opened or a telescopic portion is made to slightly extend from the "storage state", is spread to be larger than that in the "storage state", and can be employed for radiation irradiation.

Alternatively, in the monitor image display method for a radiation-irradiation device according to the invention, in a case in which the radiation source holding unit is to take a non-storage state where the radiation source holding unit is unfolded for radiation irradiation and a storage state where radiation irradiation is not performed, a condition in which the radiation source holding unit is in the non-storage state may be set as the first condition and a condition in which the radiation source holding unit is in the storage state and a travel speed of the radiation-irradiation device is equal to or higher than a predetermined speed may be set as the second condition.

Further, it is preferable that the monitor image display method for a radiation-irradiation device according to the invention further includes switching an image, which is to be displayed on the monitor, to the irradiation-direction image or the front image in accordance with a travel speed of the radiation-irradiation device.

In a case in which the switching is performed, more specifically, in a case in which the travel speed is equal to or higher than the predetermined speed, it is preferable that the front image is displayed on the monitor.

Further, in a case in which the switching is performed, more specifically, in a case in which the travel speed of the radiation-irradiation device is lower than the predetermined speed, it is preferable that the irradiation-direction image is displayed on the monitor.

Furthermore, in a case in which the switching is performed, more specifically, in a case in which a time while the travel speed of the radiation-irradiation device is lower than the predetermined speed exceeds a predetermined time, the irradiation-direction image may be displayed on the monitor. In a case in which a time while the travel speed is lower than the predetermined speed is equal to or shorter than the predetermined time, the front image may be displayed on the monitor.

Moreover, in a case in which the switching is performed, more specifically, in a case in which the travel speed of the radiation-irradiation device is lower than the predetermined speed and a predetermined additional condition is satisfied, the irradiation-direction image may be displayed on the monitor.

In a case in which the switching is performed, more specifically, in a case in which a time while the travel speed of the radiation-irradiation device is lower than the predetermined speed exceeds a predetermined time and a predetermined additional condition is satisfied, the irradiation-direction image may be displayed on the monitor.

Examples of the additional condition include a condition in which a power source of the radiation image recording medium is turned on.

Further, the additional condition may be a condition in which the radiation-irradiation device detects the radiation image recording medium.

Furthermore, the additional condition may be a condition in which a trigger signal for making the radiation-irradiation device be in an imaging preparation state is generated from a console of the radiation-irradiation device.

In addition, in a case in which an exposure switch of which a pressing operation is performed by two stages is used as an exposure switch for driving the radiation source, the additional condition may be a condition in which a first-stage pressing operation of the exposure switch is performed.

Further, in the monitor image display method for a radiation-irradiation device according to the invention, it is preferable that one optical camera, of which a direction is changed to a case in which the front image is to be taken and a case in which the irradiation-direction image is to be taken, is used as the optical camera.

Alternatively, a dedicated optical camera for taking the front image and a dedicated optical camera for taking the irradiation-direction image may be used as the optical camera.

It is preferable that cameras of which at least one of imaging angles of view, resolutions, frame rates, and shutter speeds are different from each other are used as the dedicated optical camera for taking the irradiation-direction image and the dedicated optical camera for taking the front image.

A radiation-irradiation device according to the invention irradiates a radiation image recording medium with radiation to take a radiation image and is adapted to be capable of traveling. The radiation-irradiation device includes: a radiation source that generates radiation; a radiation source holding unit that is capable of at least setting the radiation source to a direction in which the radiation source irradiates the radiation image recording medium with radiation at the time of radiation irradiation and setting the radiation source to a vertically downward direction; at least one optical camera that is capable of taking at least a front image showing a field of view on a front side in a traveling direction of the radiation-irradiation device and an irradiation-direction image showing a field of view in a radiation-irradiation direction at the time of radiation irradiation; a monitor that displays the image taken by the optical camera; direction detecting unit that detects a direction of the radiation source; and display control unit that displays the irradiation-direction image on the monitor in a case in which the direction of the radiation source detected by the direction detecting unit is set to a direction other than the downward direction, displaying the irradiation-direction image on the monitor in a case in which the radiation source is set to the downward direction and a first condition is satisfied, and displaying the front image on the monitor in a case in which the radiation source is set to the downward direction and a second condition different from the first condition is satisfied.

In the radiation-irradiation device of the invention, it is preferable that the radiation source holding unit may be to take a non-storage state where the radiation source holding unit is unfolded for radiation irradiation and a storage state where radiation irradiation is not performed. The radiation-irradiation device may further include: state detecting unit that detects which of the non-storage state and the storage state the radiation source holding unit is in; and speed detecting unit that detects a travel speed of the radiation-irradiation device. The display control unit may use a condition, in which the state of the radiation source holding unit detected by the state detecting unit is the non-storage state, as the first condition and may use a condition, in which the state of the radiation source holding unit detected by the state detecting unit is the storage state, as the second condition.

Alternatively, in the radiation-irradiation device of the invention, the radiation source holding unit may be to take a non-storage state where the radiation source holding unit is unfolded for radiation irradiation and a storage state where radiation irradiation is not performed. The radiation-irradiation device may further include: state detecting unit that detects which of the non-storage state and the storage state the radiation source holding unit is in; and speed detecting unit that detects a travel speed of the radiation-irradiation device. The display control unit may use a condition, in which the state of the radiation source holding unit detected by the state detecting unit is the non-storage state, as the first condition and may use a condition, in which the state of the radiation source holding unit detected by the state detecting unit is the storage state and the travel speed detected by the speed detecting unit is equal to or higher than a predetermined speed, as the second condition.

Further, it is preferable that the radiation-irradiation device of the invention further includes speed detecting unit that detects a travel speed of the radiation-irradiation device, and the display control unit switches an image, which is to be displayed on the monitor, to the irradiation-direction image or the front image in accordance with the travel speed of the radiation-irradiation device detected by the speed detecting unit.

In a case in which the display control unit performs the switching, more specifically, in a case in which the travel speed of the radiation-irradiation device is equal to or higher than a predetermined speed, it is preferable that the display control unit displays the front image on the monitor.

In a case in which the display control unit performs the switching, more specifically, in a case in which the travel speed of the radiation-irradiation device is lower than the predetermined speed, it is preferable that the display control unit displays the irradiation-direction image on the monitor.

Alternatively, in a case in which the display control unit performs the switching, more specifically, in a case in which a time while the travel speed of the radiation-irradiation device is lower than the predetermined speed exceeds a predetermined time, the display control unit may display the irradiation-direction image on the monitor. In a case in which a time while the travel speed of the radiation-irradiation device is lower than the predetermined speed is equal to or shorter than the predetermined time, the display control unit may display the front image on the monitor.

In a case in which the display control unit performs the switching, more specifically, in a case in which the travel speed of the radiation-irradiation device is lower than the predetermined speed and a predetermined additional condition is satisfied, it is preferable that the display control unit displays the irradiation-direction image on the monitor.

In a case in which the display control unit performs the switching, more specifically, in a case in which a time while the travel speed of the radiation-irradiation device is lower than the predetermined speed exceeds a predetermined time and a predetermined additional condition is satisfied, the display control unit may display the irradiation-direction image on the monitor.

Examples of the additional condition include a condition in which a power source of an electronic cassette, which is the radiation image recording medium, is turned on.

Further, the additional condition may be a condition in which the radiation-irradiation device detects the radiation image recording medium.

Furthermore, the additional condition may be a condition in which a trigger signal for setting the radiation-irradiation device to an imaging preparation state is generated from a console of the radiation-irradiation device.

In addition, in a case in which the radiation-irradiation device of the invention includes an exposure switch of which a pressing operation is performed by two stages as an exposure switch for driving the radiation source, the additional condition is a condition in which a first-stage pressing operation of the exposure switch may be performed.

Further, it is preferable that the optical camera of the radiation-irradiation device of the invention is one optical camera of which a direction is changed to a case in which the front image is to be taken and a case in which the irradiation-direction image is to be taken.

Alternatively, a dedicated optical camera for taking the front image and a dedicated optical camera for taking the irradiation-direction image may be used as the optical camera of the radiation-irradiation device of the invention.

In this case, it is preferable that the dedicated optical camera for taking the irradiation-direction image and the dedicated optical camera for taking the front image are cameras of which at least one of imaging angles of view, resolutions, frame rates, and shutter speeds are different from each other.

The radiation-irradiation device of the invention includes: direction detecting unit that detects the direction of a radiation source; and display control unit that displays the irradiation-direction image on the monitor in a case in which the direction of the radiation source detected by the direction detecting unit is set to a direction other than the downward direction, displaying the irradiation-direction image on the monitor in a case in which the radiation source is set to the downward direction and a first condition is satisfied, and displaying the front image on the monitor in a case in which the radiation source is set to the downward direction and a second condition different from the first condition is satisfied. Accordingly, according to the invention, a device operator can confirm a situation on the front side in a traveling direction in a case in which the device operator makes a radiation-irradiation device holding a radiation source travel and also can confirm a situation around a subject in a case in which the device operator takes a radiation image.

DESCRIPTION OF EMBODIMENTS

Figure 1:
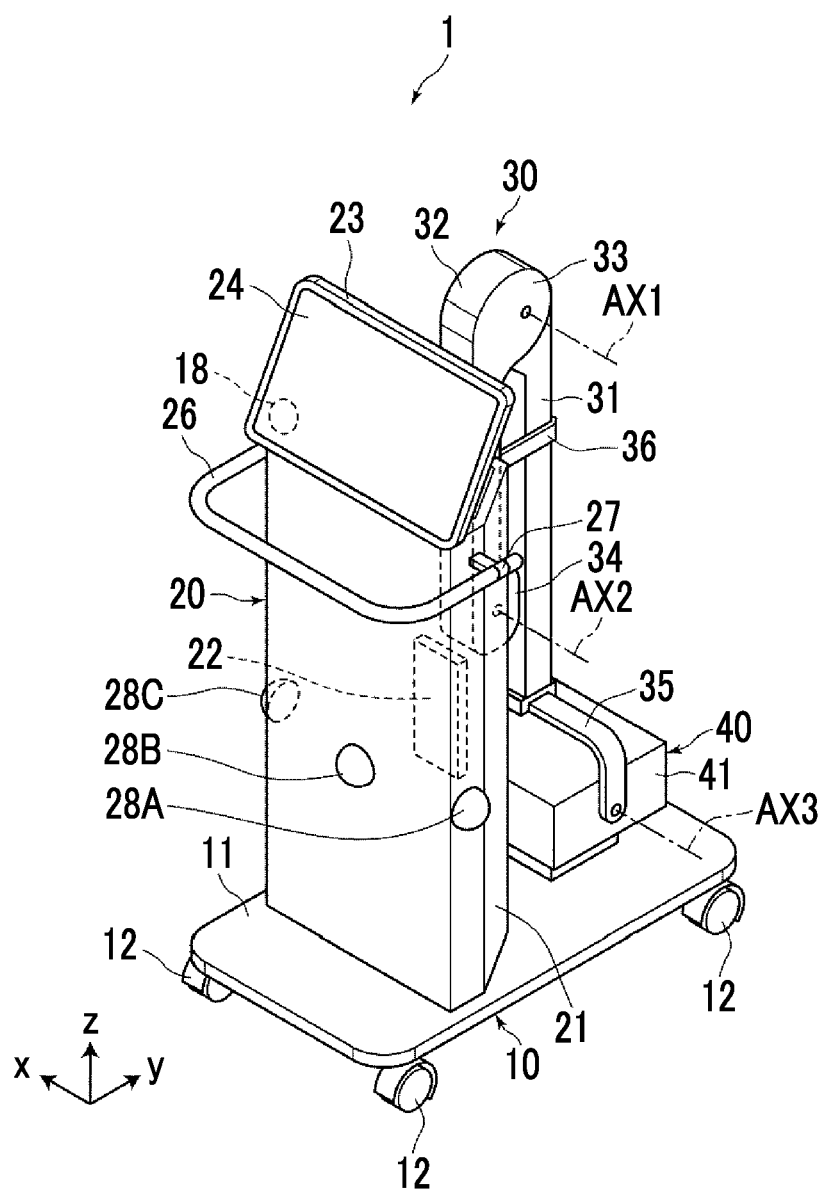
FIG. 1 is a perspective view showing the shape of the entire radiation-irradiation device according to an embodiment of the invention.
Figure 2:
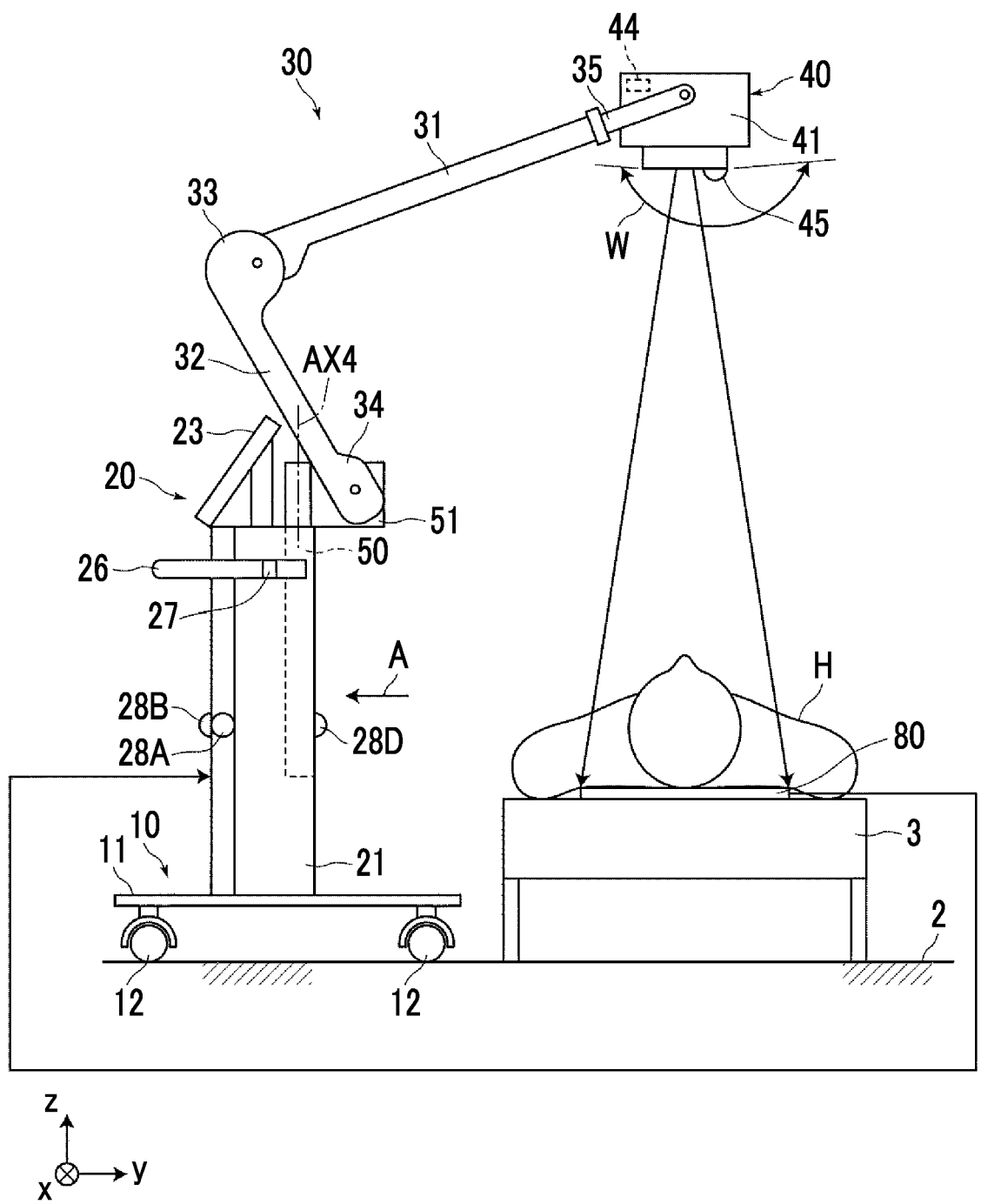
FIG. 2 is a diagram showing a state in which the radiation-irradiation device is in use.

Embodiments of the invention will be described below with reference to the drawings. FIG. 1 is a perspective view showing the shape of the entire radiation-irradiation device according to an embodiment of the invention that is not in use, and FIG. 2 is a side view showing a state in which the radiation-irradiation device is in use. In the following description, the upper side and the lower side in a vertical direction in a state in which the radiation-irradiation device is placed on a device-placement surface, such as the floor of, for example, a medical facility, are referred to as "upper" and "lower", and a direction perpendicular to the vertical direction in the same state as the state is referred to as a "horizontal" direction. Further, the vertical direction is defined as a z direction, a lateral direction of FIG. 2 is defined as a y direction, and a direction perpendicular to the plane of FIG. 2 is defined as an x direction in the following description.

As shown in FIGS. 1 and 2, the radiation-irradiation device 1 of this embodiment includes a leg unit 10, a body unit 20, an arm unit 30 serving as a radiation source holding unit, and a radiation source unit (radiation source) 40.

The leg unit 10 can travel on a device-placement surface 2, and includes a plate-like base 11 and four wheel parts 12 that are mounted on four corners of the lower surface of the base 11. As in the case of a general caster, each of the wheel parts 12 is formed of a wheel, such as a rubber tire, a revolving portion that holds the wheel so as to allow the wheel to be rotatable, and the like. The revolving portion is mounted on the base 11 so as to be revolvable about an axis, which extends in the vertical direction, in a horizontal plane. Accordingly, the leg unit 10 is adapted to be capable of traveling on the device-placement surface 2 in an arbitrary direction.

The body unit 20 is installed on the leg unit 10, and includes a housing 21. A control unit 22, which controls the drive of the radiation-irradiation device 1, and a battery (not shown) are received in the housing 21. The control unit 22 is a unit that is used to control not only the dose, the irradiation time, and the like of radiation generated from the radiation source unit 40 but also various operations of the radiation-irradiation device 1. The control unit 22 is formed of, for example, a computer in which a program for control is installed, dedicated hardware, or a combination of both the computer and the dedicated hardware. Further, a monitor 23 in which a speaker 18 is built is mounted on the upper surface of the housing 21. A handle 26, which is used to push or pull the radiation-irradiation device 1, is mounted on the upper portion of the housing 21 through an adapter 27. Furthermore, cameras 28A, 28B, 28C, and 28D, which are used to take an omnidirectional image of the device 1, are mounted on the right side surface, the rear surface, the left side surface, and the front surface of the body unit 20, respectively. For example, a digital video camera, which outputs digital signals representing a taken video, is used as each of these cameras 28A to 28D. However, the camera is not limited thereto, and a digital still camera may be applied.

The monitor 23 serving as display unit is formed of a liquid crystal panel or the like, and displays a radiation image that is acquired from the imaging of a subject H and various kinds of information that is required for the control of the device 1. Further, the monitor 23 includes a touch panel type input unit 24, and receives the input of various commands required for the operation of the device 1. The input unit 24 functions as a console (operator console) that is used to command various operations of the radiation-irradiation device 1 as described later. The monitor 23 is mounted on the upper surface of the body unit 20 so that the inclination and the rotational position of the monitor 23 are changeable.

The arm unit 30 is held on the body unit 20. In detail, the arm unit 30 is held on the surface of the body unit 20 opposite to the handle 26, that is, a right surface 20A of the body unit 20 in FIG. 2. The arm unit 30 is adapted to be capable of being raised and lowered relative to the body unit 20 by a raising/lowering mechanism 50 that is formed of, for example, a pantograph mechanism or the like. The arm unit 30 includes a first arm 31, a second arm 32 a first rotational moving portion 33, a second rotational moving portion 34, and a radiation source holding part 35. The radiation source unit 40 is held at the distal end of the first arm 31 through the radiation source holding part 35. In the following description, an end portion of the first arm 31 close to the radiation source unit 40 is referred to as an upper end portion and an end portion of the first arm 31 close to the second arm 32 is referred to as a lower end portion. Further, an end portion of the second arm 32 close to the first arm 31 is referred to as an upper end portion and an end portion of the second arm 32 close to the body unit 20 is referred to as a lower end portion.

The first and second arms 31 and 32 are connected to each other by the joint-like first rotational moving portion 33 so as to be rotationally movable about a rotational movement axis AX1. The rotational movement axis AX1 is an axis extending in the x direction. The first arm 31 is rotationally moved about the rotational movement axis AX1 so that an angle between the first and second arms 31 and 32 is changed. The first rotational moving portion 33 holds both the first and second arms 31 and 32 so that the first arm 31 is rotationally moved relative to the second arm 32 through a friction mechanism. For this reason, the first arm 31 is rotationally movable in a case in which an external force, which is strong to some extent, is applied to the first arm 31, and maintains an angle relative to the second arm 32 without being rotationally moved as long as an external force is not applied to the first arm 31.

The second arm 32 is connected to an adapter 51, which is mounted on the upper end portion of the raising/lowering mechanism 50, through the joint-like second rotational moving portion 34 so as to be rotationally movable about a rotational movement axis AX2. The rotational movement axis AX2 is an axis extending in the x direction. The second arm 32 is rotationally moved in a yz plane about the rotational movement axis AX2 so that an angle between the second arm 32 and the surface of the body unit 20 on which the arm unit 30 is held is changed. The second rotational moving portion 34 holds both the second arm 32 and the adapter 51 so that the second arm 32 is rotationally moved relative to the adapter 51 through a friction mechanism. For this reason, the second rotational moving portion 34 is rotationally movable in a case in which an external force, which is strong to some extent, is applied to the second rotational moving portion 34, and maintains an angle relative to the body unit 20 without being rotationally moved as long as an external force is not applied to the second rotational moving portion 34.

Figure 3:
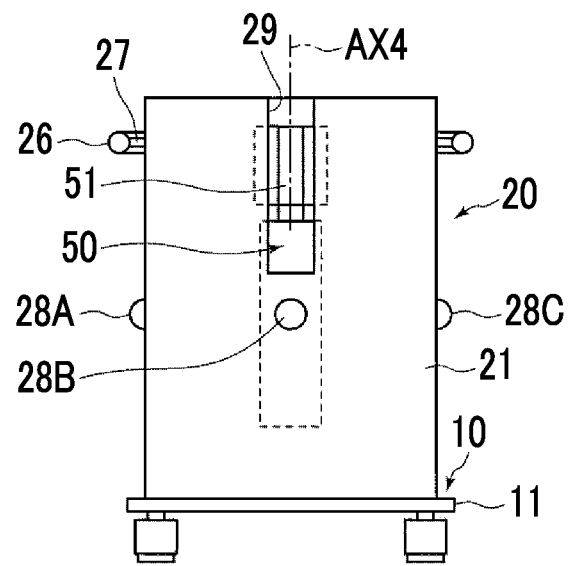
FIG. 3 is a diagram viewed in the direction of an arrow A of FIG. 2.

FIG. 3 is a diagram viewed in the direction of an arrow A of FIG. 2. As shown in FIG. 3, a groove 29, through which the adapter 51 can pass at the time of an operation for raising and lowering the arm unit 30 performed by the raising/lowering mechanism 50, is formed on the right surface of the body unit 20 in FIG. 2. For illustration, the monitor 23 and the arm unit 30 are not shown in FIG. 3.

The radiation source holding part 35 is formed in a substantially U shape, and is mounted on the distal end of the first arm 31. The radiation source unit 40 is connected to the distal end of the first arm 31 through the radiation source holding part 35 so as to be rotationally movable about a rotational movement axis AX3. The rotational movement axis AX3 is an axis extending in the x direction. The radiation source unit 40 is rotationally moved about the rotational movement axis AX3 so that an angle between the radiation source unit 40 and the first arm 31 is changed. The radiation source holding part 35 holds both the radiation source unit 40 and the first arm 31 so that the radiation source unit 40 is rotationally moved relative to the first arm 31 through a friction mechanism. For this reason, the radiation source unit 40 is rotationally movable in a case in which an external force, which is strong to some extent, is applied to the radiation source unit 40, and maintains an angle relative to the first arm 31 without being rotationally moved as long as an external force is not applied to the radiation source unit 40.

Furthermore, the adapter 51 is connected to the raising/lowering mechanism 50 so as to be rotationally movable about a rotational movement axis AX4. The rotational movement axis AX4 is an axis extending in the z direction. The adapter 51 is rotationally moved in an xy plane about the rotational movement axis AX4. In a case in which the adapter 51 is rotationally moved in this way, the entire arm unit 30 is rotationally moved in the xy plane. The adapter 51 holds both the second arm 32 and the raising/lowering mechanism 50 so that the second arm 32 is rotationally moved relative to the raising/lowering mechanism 50 through a friction mechanism. For this reason, the arm unit 30 connected to the adapter 51 is rotationally movable in a case in which an external force, which is strong to some extent, is applied to the arm unit 30, and maintains a rotational movement position thereof in the xy plane without being rotationally moved as long as an external force is not applied to the arm unit 30.

As described above, in this embodiment, each of the rotational movement of the first arm 31 relative to the second arm 32, the rotational movement of the second arm 32 relative to the body unit 20 in the yz plane, the rotational movement of the radiation source unit 40 relative to the first arm 31, and the rotational movement of the entire arm unit 30 relative to the raising/lowering mechanism 50 in the xy plane is achieved through the friction mechanism. However, rotational movement positions may be fixed by publicly known lock mechanisms. In this case, it is possible to rotationally move the first arm 31, the second arm 32, the radiation source unit 40, and the entire arm unit 30 by releasing the lock mechanisms. Further, it is possible to fix the rotational movement positions by locking the lock mechanisms at desired rotational movement positions.

Here, in a case in which the radiation-irradiation device 1 shown in FIG. 1 is not in use, the arm unit 30 is positioned at an initial position. The initial position of the arm unit 30 is a position where the entire arm unit 30 is present so as to be away from the raising/lowering mechanism 50 in the y direction and is positioned at the lowest position among the positions where the arm unit 30 is positioned in the vertical direction by the raising/lowering mechanism 50 in a state in which the first and second arms 31 and 32 are folded. Particularly, in this embodiment, the initial position is set to the position of the arm unit 30 in a state in which the first and second arms 31 and 32 are folded to a limit where the first and second arms 31 and 32 are not rotationally moved any more as shown in FIG. 1. At the initial position, the second arm 32 is in a state in which the first rotational moving portion 33 is positioned above the second rotational moving portion 34.

Here, a position where the entire arm unit 30 is present so as to be away from the raising/lowering mechanism 50 in the +y direction is referred to as the initial rotational movement position of the arm unit 30. The +y direction is a right direction in FIG. 2. The arm unit 30 is rotationally movable about the rotational movement axis AX4 from the initial rotational movement position in the xy plane as described above. The rotational movement is performed about the rotational movement axis AX4 in the range of 45° in a clockwise direction to 45° in a counterclockwise direction.

The first and second arms 31 and 32 are fastened to each other by a fastening belt 36 at the initial position. For example, one end portion of the fastening belt 36 is mounted on the second arm 32 and a hook-and-loop fastener is mounted on the other end portion of the fastening belt 36. A hook-and-loop fastener corresponding to the hook-and-loop fastener of the fastening belt 36 is mounted on the surface of the first arm 31 opposite to the surface of the first arm 31 shown in FIG. 1. Further, the fastening belt 36 is put around the first arm 31 from the right surface of the first arm 31 in FIG. 1 to the opposite surface of the first arm 31 to connect the hook-and-loop fastener of the fastening belt 36 to the hook-and-loop fastener mounted on the first arm 31. Accordingly, the first arm 31 is not rotationally moved relative to the second arm 32 at the initial position.

Figure 4:
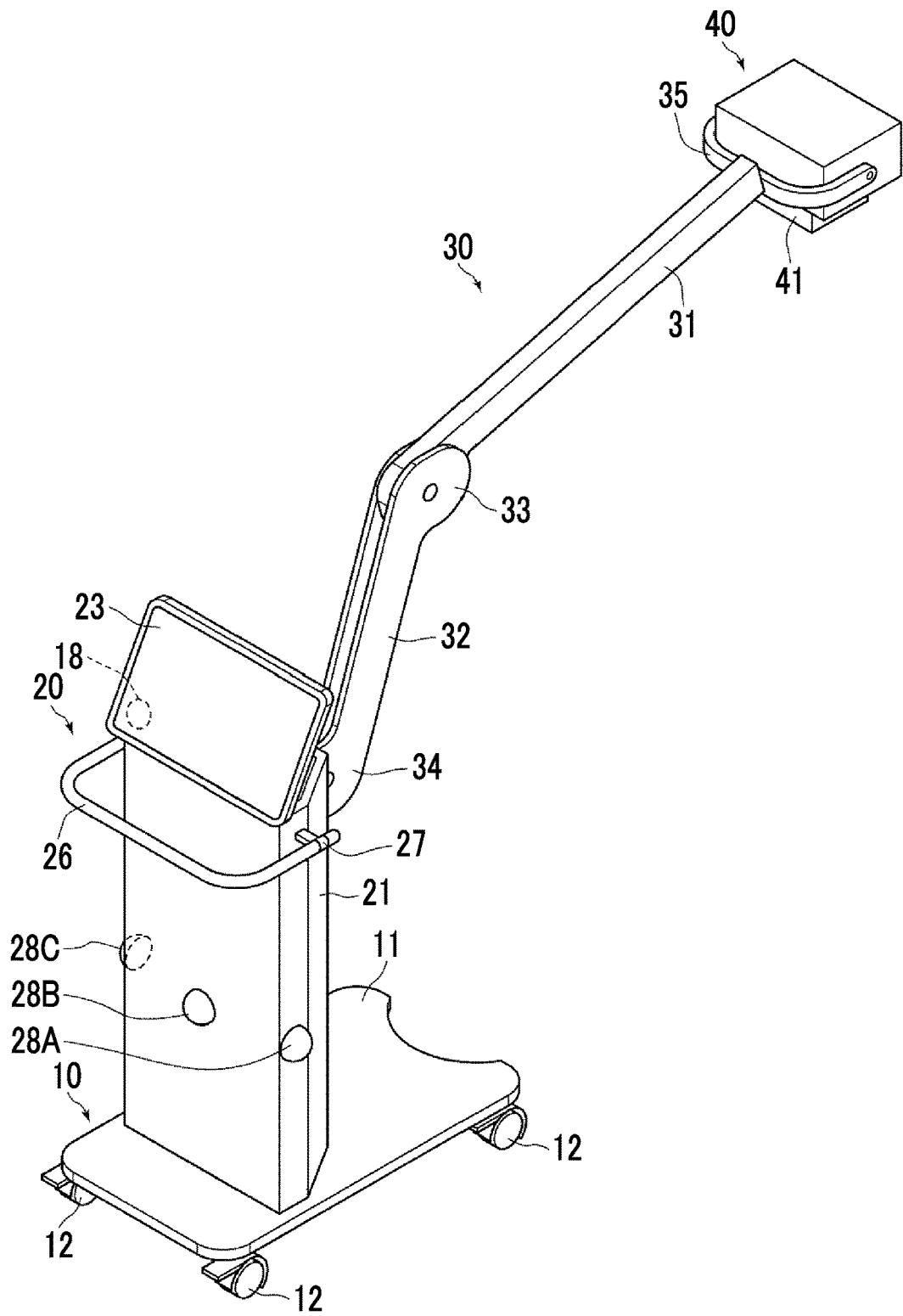
FIG. 4 is a perspective view showing a state in which the radiation-irradiation device is in use.

In a case in which the radiation-irradiation device 1 is used, the arm unit 30 is shifted from the initial position to a use position at which the first and second arms 31 and 32 are unfolded. FIG. 4 shows the radiation-irradiation device 1 of which the arm unit 30 is set to one example of the use position.

The radiation source unit 40 has a structure where a radiation source, a collimator for narrowing the irradiation range of radiation, a direction sensor 44 for detecting the direction of the radiation source unit 40 (a direction in which radiation is emitted), and the like are received in a housing 41. The radiation source includes, for example, an X-ray tube, a booster circuit, cooling unit that cools the X-ray tube, and the like. The direction sensor 44 is formed of, for example, an acceleration sensor or the like. Further, a camera 45, which is an optical camera, is connected to the radiation source unit 40. The "optical camera" is a camera that has sensitivity for visible light or infrared light and takes an image formed by a lens optical system. Particularly, a digital video camera, which outputs digital signals representing a taken video, is applied in this embodiment. However, the camera is not limited thereto, and a digital still camera may be applied. The camera 45 includes an actuator (not shown) that makes an imaging system be rotationally moved, and is adapted to be capable of appropriately changing an imaging direction in an angular range, which is shown by an arrow W of FIG. 2, by the drive of the actuator. The rotational movement of the imaging system is performed about an axis parallel to the rotational movement axis AX3 of the above-mentioned radiation source unit 40. Further, the emission of radiation from the radiation source of the radiation source unit 40 is performed by a command that is input from the input unit 24 of the monitor 23 by an operator.

The input unit 24 is used to input information that is required to perform various operations of the radiation-irradiation device 1, and forms a console (operator console), which is used to perform the management of imaging orders, the image processing of a taken image, the display of the taken image, and the like, together with the control unit 22 and the monitor 23.

In this embodiment, in a case in which the radiation image of a subject H is to be taken, a radiation detector 80 is disposed under a subject H supine on a bed 3 as shown in FIG. 2 and is irradiated with radiation, such as, X-rays, emitted from the radiation source of the radiation source unit 40 and passing through the subject H.

Figure 5:
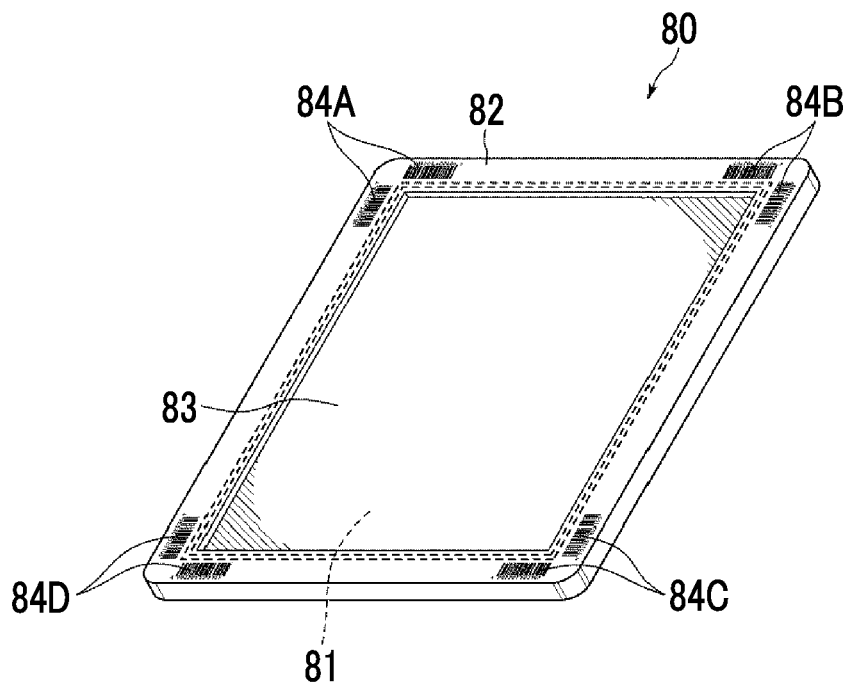
FIG. 5 is a perspective view showing the appearance of a radiation detector viewed from a front surface that is a radiation-irradiation side.

The radiation detector 80 will be briefly described here with reference to FIG. 5. FIG. 5 is a perspective view showing the appearance of the radiation detector viewed from a front surface that is a radiation-irradiation side. As shown in FIG. 5, the radiation detector 80 of this embodiment is a cassette-type radiation detector that includes an image detection unit 81 serving as a radiation image recording medium and a housing 82 receiving the image detection unit 81. As well known, the image detection unit 81 includes a scintillator (phosphor) that converts incident radiation into visible light and a thin-film-transistor (TFT) active matrix substrate. A rectangular imaging region in which a plurality of pixels for accumulating electric charges corresponding to visible light emitted from the scintillator are arranged is formed on the TFT active matrix substrate. In the radiation detector 80, the image detection unit 81 is a radiation image recording medium. However, for convenience' sake, the entire radiation detector 80 may also be called as a radiation image recording medium in this specification.

An imaging control unit, which includes a gate driver, a signal processing circuit, and the like, and the like are built in the housing 82 in addition to the image detection unit 81. The gate driver applies gate pulses to a gate of a TFT to switch the TFT. The signal processing circuit converts electric charges, which are accumulated in the pixels, into analog electrical signals, which represent an X-ray image, and outputs the analog electrical signals. Further, the housing 82 has substantially the same size as, for example, a film cassette, an imaging plate (IP) cassette, or a computed radiography (CR) cassette that is based on International Organization for Standardization (ISO) 4090:2001.

Markers 84A to 84D, which represent identification information for identifying the radiation detector 80, are given to four corners of a front surface 82A of the housing 82. In this embodiment, each of the markers 84A to 84D is formed of two bar codes orthogonal to each other. Further, the markers 84A to 84D may be adapted to transmit identification information by radio.

Next, an operation in a case in which a radiation image is not yet taken by the radiation-irradiation device 1 of this embodiment will be described. In the state which is shown in FIG. 1 and in which the radiation-irradiation device 1 is not in use, that is, in a state in which the arm unit 30 is stored, the radiation-irradiation device 1 is transported to a use position while being made to travel on the device-placement surface 2, such as the floor of a hospital, by the wheel parts 12 of the leg unit 10. The transport of the radiation-irradiation device 1 is performed by a transport force for pushing or pulling the radiation-irradiation device 1 that is applied by an operator (device user) while the operator holds the handle 26.

Here, "a state in which the arm unit 30 is stored" is a state in which the arm unit 30 is positioned at the above-mentioned initial position. In a case corresponding to emergency care or the like, the radiation-irradiation device 1 may be carried to the use position in the same manner as described above in a state in which the arm unit 30 is unfold. Since each of the wheel parts 12 is revolvably mounted on the base 11 as described above, the radiation-irradiation device 1 can be moved in a front-back direction and the lateral direction and can also be moved along a large curve. In addition, the radiation-irradiation device 1 can also revolve at that position. Accordingly, the radiation-irradiation device 1 can be quickly transported to a use position in a state in which the radiation-irradiation device 1 revolves in a small radius.

The taking of a radiation image is performed on the subject H who is supine on, for example, the bed 3 as shown in the above-mentioned FIG. 2. In a case in which the radiation-irradiation device 1 is to be set close to the subject H, the radiation-irradiation device 1 can also be moved in the height direction of the subject H by the wheel parts 12. Accordingly, the radiation-irradiation device 1 can be easily set at the optimum position.

Figure 6:
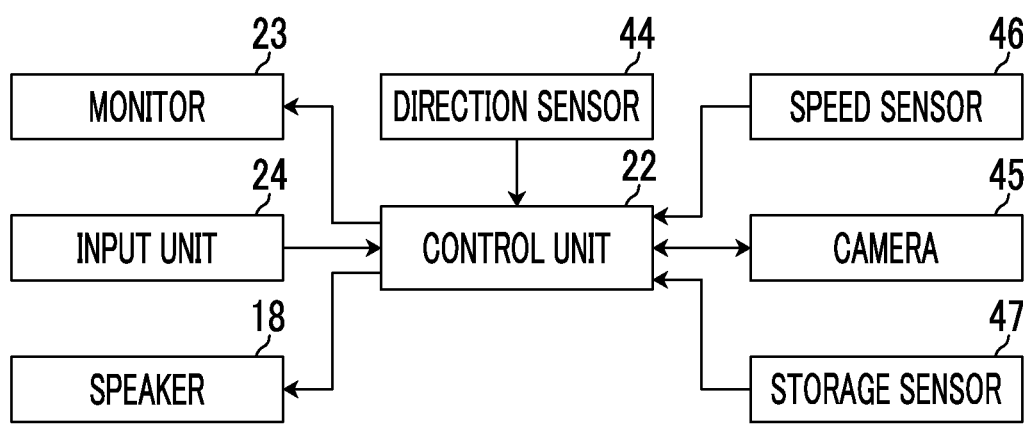
FIG. 6 is a block diagram showing the electrical configuration of a part of the radiation-irradiation device.

Next, a monitor image display method for a radiation-irradiation device according to an embodiment of the invention will be described. FIG. 6 is a block diagram showing the electrical configuration of a portion that relates to the control of the monitor image display method. The control unit 22, the camera 45 that is connected to the control unit 22, the monitor 23 that receives image signals output from the camera 45 and sent through the control unit 22, the speaker 18 that receives voice signals output by the control unit 22, and the input unit 24 that is used to input various commands to the control unit 22 are provided in the configuration of FIG. 6. Further, the detection signal of the direction sensor 44 for detecting the direction of the radiation source unit 40, the detection signal of a speed sensor 46 for detecting the travel speed of the radiation-irradiation device 1, and the detection signal of a storage sensor 47 for detecting that the arm unit 30 is in a storage state are input to the control unit 22. The control unit 22 forms display control unit of the invention.

Next, the setting of the direction of the camera 45, that is, a direction in which imaging is performed and the display of an image taken by the camera 45 will be described with reference to flow charts of FIGS. 7 and 8. Since the travel of the radiation-irradiation device 1 is performed in this embodiment by the push of the handle 26 of FIG. 1, which is performed by an operator, the traveling direction is the direction of an arrow y of FIG. 1. Further, the direction of the camera 45 is set to a forward direction (a direction facing the front side in the traveling direction of the radiation-irradiation device 1) to be described later in a case in which processing shown in the flow charts of FIGS. 7 and 8 is not yet started.

Figure 7:
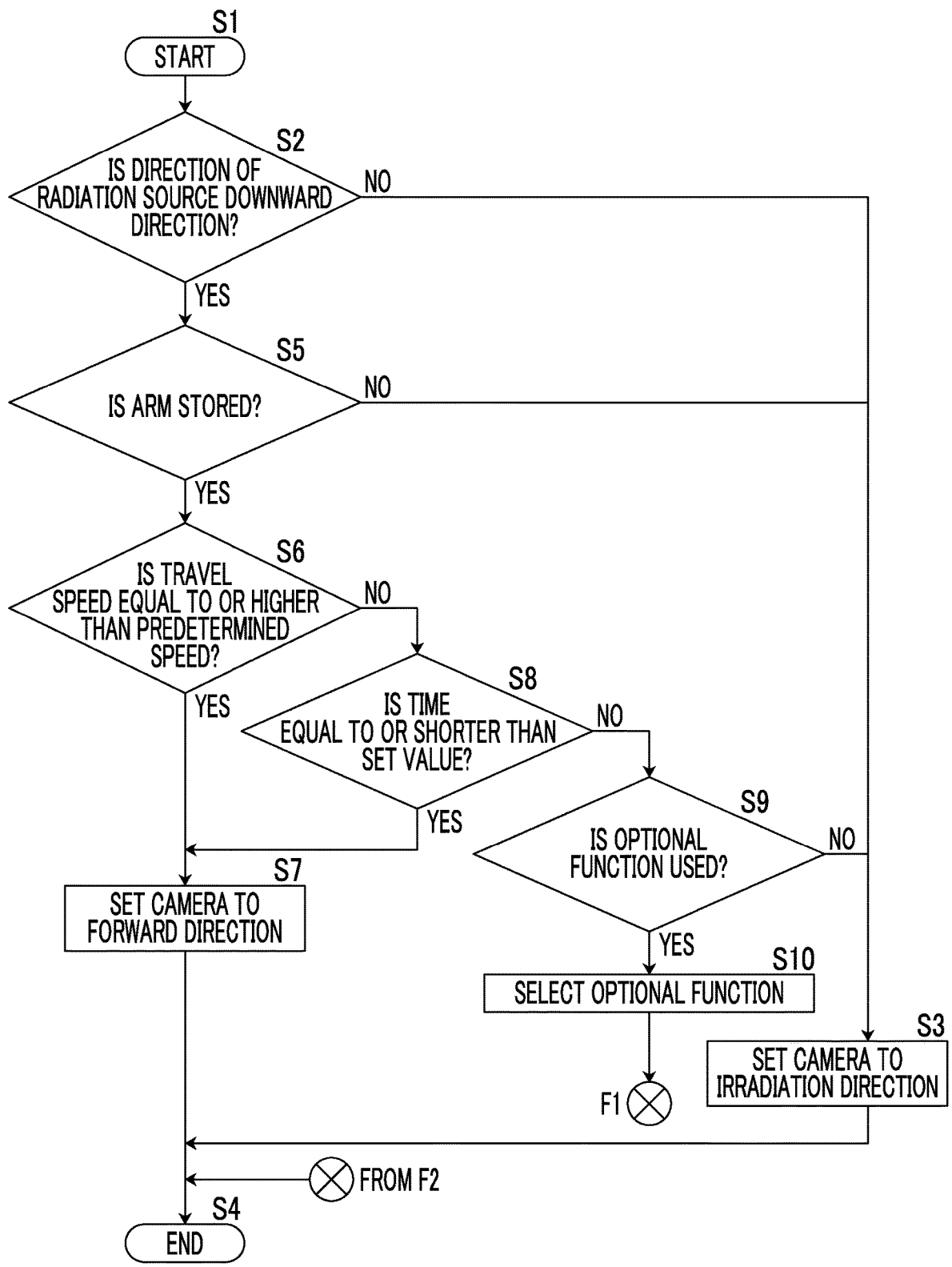
FIG. 7 is a flow chart showing the flow of a part of processing of a monitor image display method according to an embodiment of the invention.
Figure 8:
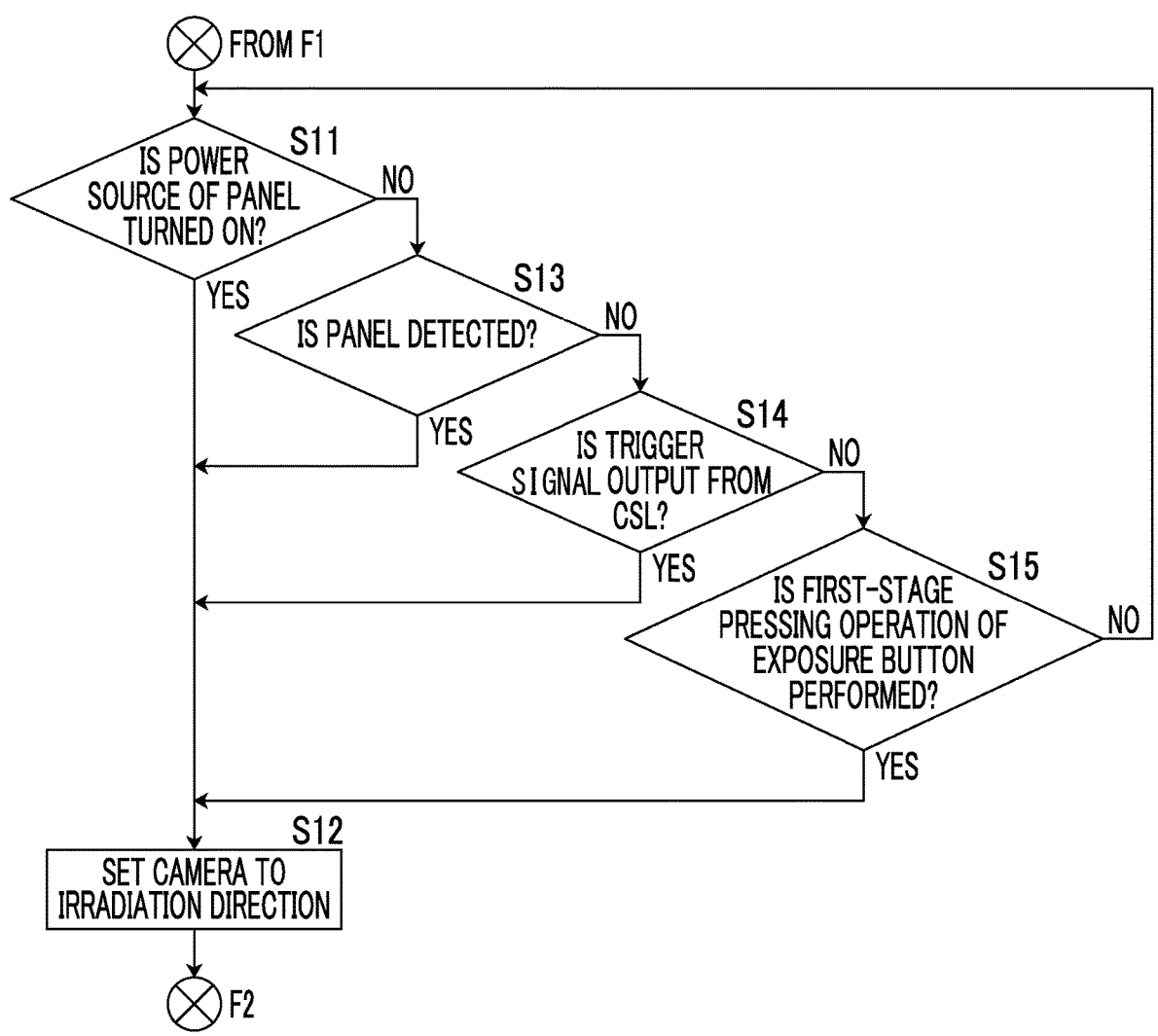
FIG. 8 is a flow chart showing the flow of a part of processing of the monitor image display method according to the embodiment of the invention.

As shown in FIG. 7, processing is started first in Step S1, and the control unit 22 then determines whether or not the direction of the radiation source unit 40 represented by an output signal of the direction sensor 44 is a downward direction in the next step S2. If the determination of "NO" is made, that is, if it is determined that the direction of the radiation source unit 40 is not the downward direction, the control unit 22 sets the direction of the camera 45 to a radiation-irradiation direction (hereinafter, referred to as an irradiation direction) in the next step S3 and ends processing in Step S4. In more detail, a drive command signal is input to the above-mentioned actuator of the camera 45 from the control unit 22 and the actuator makes the imaging system of the camera 45 be rotationally moved, so that the setting of the direction of the camera 45 is performed.

In a case in which the radiation-irradiation device 1 is made to travel to be transported, it is strongly required that the radiation source unit 40 is set to the downward direction to prevent a person, which is in the vicinity of a transport path, and the like from being irradiated with radiation generated by mistake. Accordingly, in a case in which the radiation source unit 40 is not set to the downward direction, it is thought that the radiation-irradiation device 1 is not being transported and the radiation source unit 40 is set to a direction other than the downward direction, for example, a rightward direction or the like in FIG. 2 to prepare the imaging (imaging at a seated posture or the like) of a subject H and the direction of the camera 45 is set to the irradiation direction. Therefore, an irradiation-direction image, that is, the image of a field of view in the radiation-irradiation direction where a radiation image is to be taken from now on, particularly, the image of a field of view in the radiation-irradiation direction including a radiation-irradiation field is taken by the camera 45, and the taken image is displayed on the monitor 23.

The "downward direction" includes not only a case in which the imaging direction is exactly a vertically downward direction but also a case in which the imaging direction deviates from the vertically downward direction by an angle of, for example, about 10° in an arbitrary direction.

Figure 10:
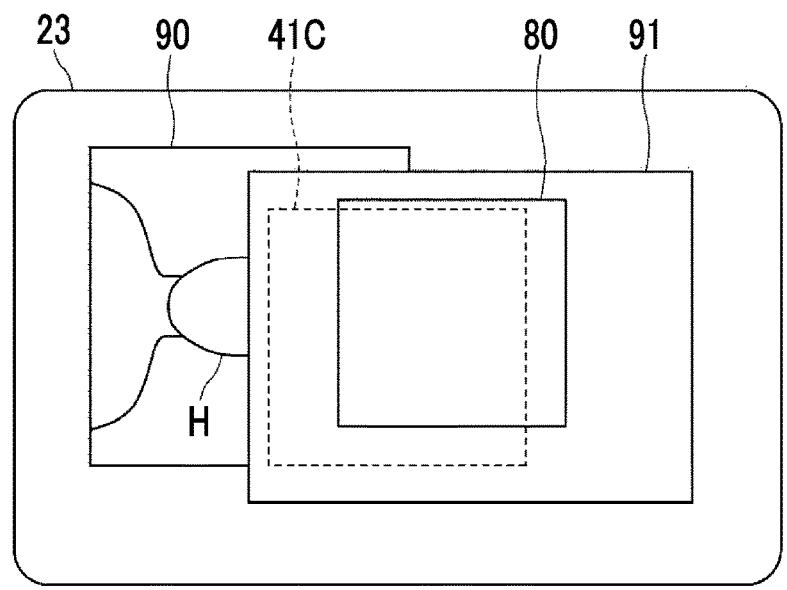
FIG. 10 is a schematic diagram showing another example of the monitor display image of the radiation-irradiation device.

FIG. 10 shows an example of the irradiation-direction image to be displayed on the monitor 23. In this embodiment, a processed image 91 obtained in a collimator-frame display mode where the radiation detector 80 and a collimator frame 41C of the radiation source unit 40 are shown is displayed in addition to an optical image 90 obtained in a cassette-position detection mode where the subject H and the markers 84A to 84D (see FIG. 5) of the radiation detector 80 are shown as they are.

For example, the markers 84A to 84D, which are given to the housing 82 of the radiation detector 80 as described above, are detected through image processing, so that the position of the radiation detector 80 in the processed image 91 can be recognized. In addition, the markers 84A to 84D, which transmit identification information by radio as described above, can be detected by a receiver (not shown) provided on the radiation-irradiation device 1 and the position of the radiation detector 80 can also be recognized on the basis of the detection information of the receiver. Further, the position of the collimator frame 41C is calculated on the basis of, for example, the specifications of the radiation source unit 40 and the detected position of the radiation source unit 40 (which can be detected from the state of the arm unit 30). The display of the positions of the radiation detector 80 and the collimator frame 41C, which are obtained in this way, is overlaid on an optical image that is taken by the camera 45.

The operator can perform an operation relating to the taking of a radiation image, such as an operation for rotationally moving the arm unit 30 to set the position of the radiation source unit 40, and can also confirm whether or not the radiation source unit 40 is set to an appropriate position, with reference to the images 90 and 91 that are displayed on the monitor 23 as described above. In more detail, the operator can prevent the subject H from being unnecessarily exposed to radiation by matching the position of the collimator frame 41C with the radiation detector 80.

Returning to FIG. 7, if the determination of "YES" is made in Step S2, that is, if it is determined in Step S2 that the radiation source unit 40 is set to the downward direction, the control unit 22 then determines whether or not the arm unit 30 is stored in Step S5. This determination is performed on the basis of the detection signal output from the storage sensor 47 shown in FIG. 6. If it is determined that the arm unit 30 is stored, that is, if it is determined that the arm unit 30 is in the state shown in FIG. 1, the control unit 22 then determines in Step S6 whether or not the travel speed of the radiation-irradiation device 1 is equal to or higher than a preset speed. This determination is performed on the basis of the detection signal output from the speed sensor 46 shown in FIG. 6. If it is determined that the travel speed is equal to or higher than a certain speed, the control unit 22 sets the direction of the camera 45 to a direction facing the front side in the traveling direction of the radiation-irradiation device 1 (hereinafter, simply referred to as a forward direction) in Step S7. In this embodiment, the forward direction is the direction of the arrow y of FIG. 1 and faces the right side in the plane of FIG. 2 in the illustration of FIG. 2.

Accordingly, the field of view on the front side in the traveling direction of the radiation-irradiation device 1 is imaged by the camera 45, and the image of the field of view on the front side (front image) is displayed on the monitor 23. The operator can safely transport the radiation-irradiation device 1 while confirming whether or not an obstacle is present in a direction in which the radiation-irradiation device 1 travels with reference to the front image.

Figure 9:
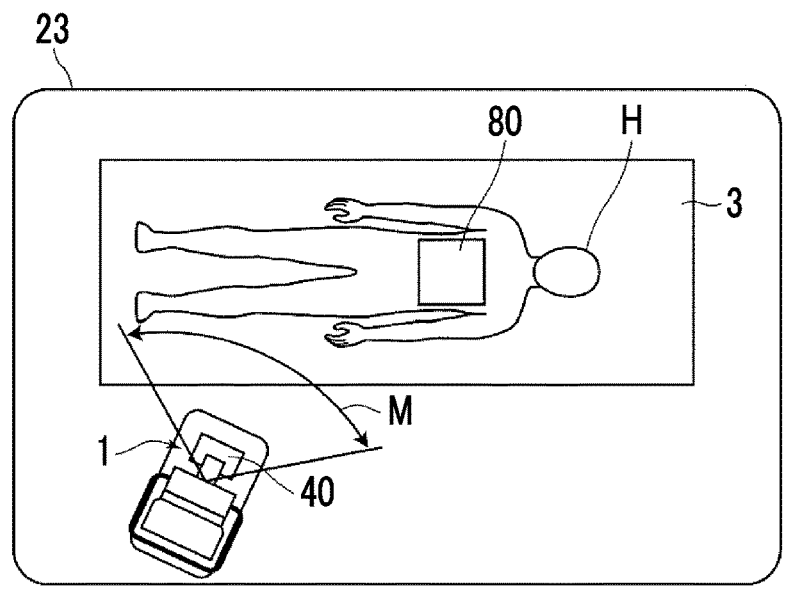
FIG. 9 is a schematic diagram showing an example of a monitor display image of the radiation-irradiation device.

An omnidirectional image of the radiation-irradiation device 1 shown in FIG. 9 may be displayed on the monitor 23 instead of the front image at a point of time when the radiation-irradiation device 1 is sufficiently close to the subject H. The omnidirectional image is obtained through reconstruction from images of the radiation-irradiation device 1, which are taken in four directions by the above-mentioned cameras 28A to 28D. It is preferable that the rotational movement range of the arm unit 30, which is shown in FIG. 9 by an arc-shaped arrow M and segments positioned on both sides of the arrow M, is displayed together with the omnidirectional image in a case in which the omnidirectional image is to be displayed. The rotational movement range of the arm unit 30 can be obtained from the use of the range of rotational movement about the rotational movement axis AX4, the length of each portion of the arm, or the like. The switching of the display of the omnidirectional image and the display of the front image may be automatically performed at a certain time interval, and or may be performed by an operator's manual operation.

Even though it is determined in Step S5 that the arm unit 30 is not stored, it is thought that the radiation-irradiation device 1 is in an imaging preparation stage. Accordingly, the control unit 22 sets the direction of the camera 45 to an irradiation direction in Step S3. Therefore, an irradiation-direction image is taken by the camera 45, and is displayed on the monitor 23. An effect obtained from the display of the irradiation-direction image is the same as the effect described above in a case in which the flow of processing proceeds to Step S3 from Step S2.

If it is determined in Step S6 that the travel speed of the radiation-irradiation device 1 is not equal to or higher (that is, lower) than a certain speed, the control unit 22 determines in Step S8 whether or not a time while the travel speed is not equal to or higher than a certain speed is equal to or shorter than a predetermined set value. If the determination of "YES" is made, it is thought that the radiation-irradiation device 1 is just temporarily stopped or decelerated and basically still travels. Accordingly, the control unit 22 then sets the direction of the camera 45 to the forward direction in Step S7 and ends processing. Therefore, the field of view on the front side in the traveling direction of the radiation-irradiation device 1 is imaged by the camera 45, and the image of the field of view on the front side (front image) is displayed on the monitor 23. An effect obtained from the display of the front image is the same as the effect described above in a case in which the flow of processing proceeds to Step S7 from Step S6.

Whether or not Step S8 is to be provided depends on the following circumstances. That is, even though the radiation-irradiation device 1 is being transported while the radiation-irradiation device 1 does not yet arrive at an imaging site, the transport of the radiation-irradiation device 1 may be temporarily stopped or decelerated. In this case, if the direction of the camera 45 is sequentially changed and an irradiation-direction image is displayed on the monitor 23, the operator is made to feel troublesome. Accordingly, if Step S8 is provided, it is possible to obtain an effect of avoiding that the camera 45 immediately faces the irradiation direction in a case in which the transport of the radiation-irradiation device 1 is temporarily stopped.

If the determination of "NO" is made in Step S8, that is, if a time while the travel speed is not equal to or higher than a certain speed exceeds a set value, the control unit 22 then determines in Step S9 whether or not to use four optional functions to be described below. The optional functions are functions to make the monitor 23 display an irradiation-direction image even though the radiation source unit 40 is set to the downward direction in a case in which a certain additional condition is satisfied.

The monitor 23 displays a question whether or not the optional functions are necessary, and the determination in Step S9 is performed on the basis of an answer to the question that is input from the input unit 24. The answer is stored in the internal memory of the control unit 22, for example, for every radiation-irradiation device 1 or every operator of the radiation-irradiation device 1, and the determination in Step S9 is performed on the basis of the memory of the answer. If the determination of "NO" is made in Step S9, that is, if it is determined that the optional functions are not used, it is thought that a radiation image is desired to be taken in a hurry. Accordingly, the control unit 22 then sets the direction of the camera 45 to an irradiation direction in Step S3. Therefore, an irradiation-direction image is taken by the camera 45, and is displayed on the monitor 23. An effect obtained from the display of the image is the same as the effect described above in a case in which the flow of processing proceeds to Step S3 from Step S2.

If the determination of "YES" is made in Step S9, that is, if it is determined that the optional functions are used, the control unit 22 then makes the monitor 23 output a display for the selection of the optional functions and allows the operator to select the optional functions in Step S10. This selection is performed using the above-mentioned input unit 24.

In a case in which the optional functions are selected, the control unit 22 then performs the processing of Steps S11 to 15 shown in FIG. 8. That is, in this embodiment, four conditions, that is, a condition in which the power source of the radiation detector 80 (written as a "panel" in FIG. 8) is turned on (Step S11), a condition in which the radiation-irradiation device 1 detects the radiation detector 80 (Step S13), a condition in which a trigger signal for making the radiation-irradiation device 1 be in an imaging preparation state is output from the above-mentioned console (written as a "CSL" in FIG. 8) formed of the input unit 24 and the like of the radiation-irradiation device 1 (Step S14), and a condition in which a first-stage pressing operation of an exposure button to be described later is performed (Step S15) are set as mutually exclusive additional conditions, and the control unit 22 sets the direction of the camera 45 to an irradiation direction (Step S12) in a case in which one of these additional conditions is satisfied. Accordingly, an irradiation-direction image is taken by the camera 45, and is displayed on the monitor 23. An effect obtained from the display of the image is the same as the effect described above in a case in which the flow of processing proceeds to Step S3 from Step S2.

As described above, in this embodiment, a condition in which the arm unit 30 serving as the radiation source holding unit is in a non-storage state is set as a first condition of the invention, and a condition in which the arm unit 30 is in a storage state and the travel speed of the radiation-irradiation device 1 is equal to or higher than a predetermined speed is set as a second condition of the invention.

If all the determination results of Steps S11, S13, S14, and S15 correspond to "NO", the flow of processing returns to Step S11. Since the processing of Steps S11, S13, S14, and S15 is performed in a case in which it is determined in Step S9 of FIG. 7 that the optional functions are used, there is a possibility that time is taken. However, the determination result of any one of Steps S11, S13, S14, and S15 finally corresponds to "YES". In a case in which the processing of Steps S11, S13, S14, and S15 is adapted to be performed in this way, the direction of the camera 45 is eventually set to an irradiation direction. However, since an original object of the processing of Steps S11, S13, S14, and S15 is to make a time interval without immediately performing the preparation of imaging as described later even though it is thought that the determination result of Step S8 of FIG. 7 corresponds to "NO" and the transport of the radiation-irradiation device 1 is stopped, the object is achieved.

The radiation source of the radiation source unit 40 can be driven by the input of a drive command from the input unit 24 of the radiation-irradiation device 1, but the exposure button mentioned above is appropriately provided on a portion other than the input unit 24. In many cases, the pressing operation of the exposure button is performed by two stages, and is adapted so that, for example, the preparation of radiation irradiation is performed by a first-stage pressing operation and the radiation source is then driven by a second-stage pressing operation. As disclosed in JP2001-333894A, the first-stage pressing operation and the second-stage pressing operation may be performed by separate exposure buttons. Generally, before the first-stage pressing operation of the exposure button can be performed, the collimator of the radiation source is driven and is set at an appropriate position.

Whether or not the above-mentioned optional functions are to be provided depends on the following circumstances. That is, even though the radiation-irradiation device 1 is being transported while the radiation-irradiation device 1 does not yet arrive at an imaging site, the transport of the radiation-irradiation device 1 may be temporarily stopped. In this case, if the direction of the camera 45 is sequentially changed and an irradiation-direction image is displayed on the monitor 23, the operator is made to feel troublesome. Accordingly, since a certain amount of time is used to perform the above-mentioned optional functions if the optional functions are provided, it is possible to obtain an effect of avoiding that the camera 45 immediately faces the irradiation direction in a case in which the transport of the radiation-irradiation device 1 is temporarily stopped.

In order to obtain the above-mentioned effect, another optional function, for example, a condition in which the rotation of the wheels of the wheel parts 12 is locked is set as an additional condition and a function to make the monitor 23 display an irradiation-direction image in a case in which the wheels are locked may be provided.

Here, the optional functions corresponding to the additional conditions particularly set in Steps S11, S13, and S14 cause an effect of supporting an operation, which relates to imaging, such as the positioning of the radiation source unit 40, by an irradiation-direction image in performing processing around the radiation detector 80 or the console in advance in a state in which the arm unit 30 is stored. On the other hand, the optional function corresponding to the additional condition set in Step S15 is a function that is more useful in acquiring the optical image of a field of view similar to the radiation-irradiation field than the above-mentioned support.

In this embodiment, four additional conditions, which are set in Steps S11, S13, S14, and S15, respectively, are set as exclusive additional conditions, and the camera 45 is made to face an irradiation direction in a case in which one of these additional conditions is satisfied. However, the camera 45 may be made to face an irradiation direction in a case in which a plurality of additional conditions of the four additional conditions are satisfied together.

Since an irradiation-direction image, which is to be taken in a case in which the optional functions are used, is an image that is obtained a point of time when the taking of a radiation image is imminent, the irradiation-direction image is often an image shown in, particularly, FIG. 10. Any one of the optical image 90 and the processed image 91, which are shown in FIG. 10, may be selected and displayed on the monitor 23. However, it is preferable that the optical image 90 is mainly displayed in the following cases.

A case in which a lock (not shown) fixing the radiation source unit 40 is released.

A case in which the arm unit 30, that is, the radiation source unit 40 is being moved.

A case in which the radiation detector 80 is being moved.

A case in which the radiation detector 80 is not present in the rotational movement range of the arm unit 30.

A case in which the position of the radiation detector 80 shown in FIG. 10 is not matched with the position of the collimator frame 41C.

On the other hand, it is preferable that the radiation-irradiation device 1 is in a front confirmation mode and, for example, the following processing or operations are performed while the above-mentioned front image is displayed on the monitor 23.

First, it is preferable that warning sound is generated in a case in which an obstacle is detected in a certain angle of view viewed from the camera 45. The warning sound can be generated from the speaker 18 shown in FIGS. 1 and 6. An obstacle can be recognized through the image processing of the front image. Alternatively, in a case in which an abnormal body is detected in the front image, whether or not the abnormal body is an obstacle may be determined by a distance sensor. In addition, a stereo (multi-eye) camera is applied as the optical camera and can also determine whether or not the abnormal body is an obstacle (three-dimensional object). The stereo camera will be described in detail later.

Here, the angle of view, which is required to detect an obstacle, is an angle of view in which the lateral distance of the field of view, for example, 5 m ahead of the camera 45 is a length double the entire width (the entire width in a state in which the arm unit 30 is stored) of the radiation-irradiation device. Further, whether or not an obstacle is present in the angle of view is determined depending on a situation at a position 5 m ahead of the camera 45. Since the above-mentioned processing is performed, it is also possible to satisfactorily detect obstacles, which are moving bodies, such as persons, and to prevent the collision with the obstacles.

It is preferable that the warning sound is changed depending on a situation in which an obstacle approaches. For example, a method of turning up the volume of the warning sound in a case in which an obstacle is present with a distance, which is equal to or shorter than a predetermined distance, is considered. Further, in the case of emergency, an announcement may be made to urge persons, who are present in the vicinity of the transport path, to evacuate. In a case in which the above-mentioned warning sound or announcement is made, an operator can avoid the collision with the obstacle by braking the wheel parts 12. Further, in a case in which the above-mentioned announcement is made, the persons, who are present in the vicinity of the transport path, can evacuate in a hurry.

In a case in which the stereo camera is applied as the camera 45, the camera 45 detects a difference in level on the placement surface for the radiation-irradiation device 1. It is preferable to notify an operator of a difference in level by a voice generated from the speaker 18 or a display on the monitor 23 in a case in which the camera 45 detects a difference in level on the placement surface for the radiation-irradiation device 1. The operator can take a proactive approach, such as a reduction in transport speed, from the notification.

Since the forward visibility of the radiation-irradiation device 1 is generally relatively good in a case in which the radiation-irradiation device 1 is the above-mentioned portable radiation-irradiation device, a method of detecting and a difference in level and notifying an operator of a difference in level is effective to prevent an accident during the transport. It can be said that the radiation-irradiation device 1 is particularly effective in a case in which the radiation-irradiation device 1 is to be transported in a hurry due to emergency.

It is preferable that the front image is taken by the camera 45 to which a shake correction mode is applied. Accordingly, it is possible to prevent a problem that a good front image cannot be acquired due to the vibration of the camera 45 during the transport of the radiation-irradiation device 1.

It is preferable that the front image is acquired with high-speed processing even if the resolution is lowered. That is, since it is dark in a hospital at the time of emergency or at night, it may be difficult to safely transport the radiation-irradiation device 1. In this case, since a front image is displayed on the monitor 23 substantially in real time if the processing speed of the front image is increased, the radiation-irradiation device 1 can be more safely transported.

Next, an example of another optical camera, which can be replaced with and used as the camera 45 of FIG. 2, will be described with reference to FIG. 11. The same components as the above-mentioned components shown in FIG. 2 are denoted in FIG. 11 by the same reference numerals as the reference numerals shown in FIG. 2, and the description thereof will be omitted as long as the same components do not particularly need to be described (The same hereinafter). In an example of FIG. 11, two cameras 45A and 45B are mounted on the radiation source unit 40. Each of these cameras 45A and 45B cannot change an imaging direction by itself, one camera 45A is mounted so as to face a direction in which a field of view in the radiation-irradiation direction can be imaged (the direction of an arrow WA), and the other camera 45B is mounted so as to face a direction in which a field of view on the front side of the radiation-irradiation device 1 can be imaged (the direction of an arrow WB) in a case in which the radiation source unit 40 is set to the downward direction. That is, the camera 45A takes an irradiation-direction image, and the camera 45B takes a front image.

Figure 12:
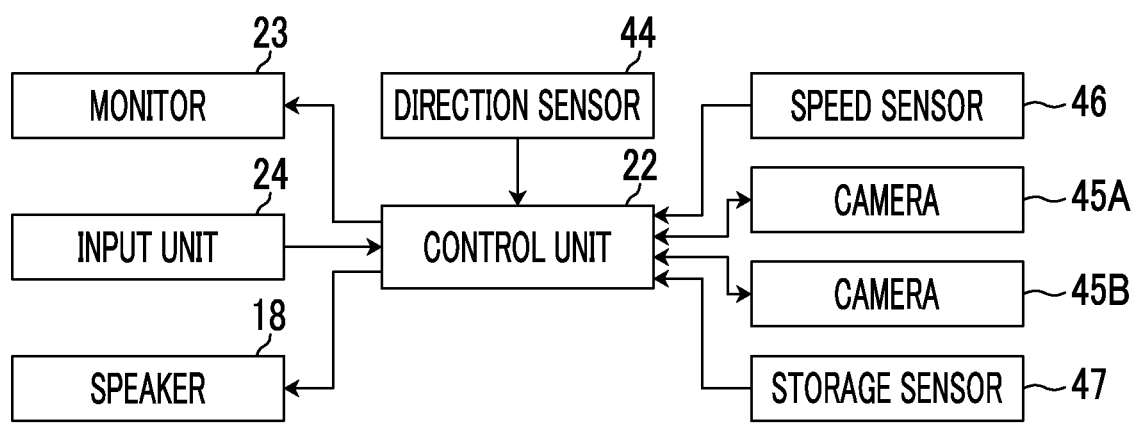
FIG. 12 is a block diagram showing the electrical configuration of a part of the radiation-irradiation device of FIG. 11.

FIG. 12 is a block diagram showing the electrical configuration of a portion that relates to the control of a monitor image display method in a case in which the cameras 45A and 45B are used. The control unit 22, the cameras 45A and 45B that are connected to the control unit 22, the monitor 23 that receives image signals output from the camera 45A or 45B and sent through the control unit 22, the speaker 18 that receives voice signals output by the control unit 22, and the input unit 24 that is used to input various commands to the control unit 22 are provided in the configuration of FIG. 12. Further, the detection signal of the direction sensor 44 for detecting the direction of the radiation source unit 40, the detection signal of the speed sensor 46 for detecting the travel speed of the radiation-irradiation device 1, and the detection signal of the storage sensor 47 for detecting that the arm unit 30 is in a storage state are input to the control unit 22. The control unit 22 forms display control unit of the invention.

In the configuration of FIG. 12, the control unit 22 is adapted to send the image signals output from the camera 45A to the monitor 23 in a case in which the control unit 22 is to make the monitor 23 display the irradiation-direction image and to send the image signals output from the camera 45B to the monitor 23 in a case in which the control unit 22 is to make the monitor 23 display the front image. Others are basically the same as the configuration of FIG. 6.

In a case in which a dedicated camera for taking an irradiation-direction image and a dedicated camera for taking a front image are provided as described above, it is preferable that the characteristics of the former camera and the characteristics of the latter camera are set to be different from each other according to the image of an object to be imaged. Examples of the characteristics of the camera include an imaging angle of view, resolution, a frame rate, a shutter speed, and the like.

More specifically, it is preferable that the imaging angle of view of a dedicated optical camera for taking an irradiation-direction image (hereinafter, referred to as a camera for an irradiation-direction image) is larger than the imaging angle of view of a dedicated optical camera for taking a front image (hereinafter, referred to as a camera for a front image). In a case in which the imaging angle of view of the camera for a front image is large, an operator can confirm the field of view on the front side in the traveling direction of the radiation-irradiation device 1 from the front image, which is displayed on the monitor 23, over a wider range and can make the radiation-irradiation device 1 more safely travel while satisfactorily confirming an obstacle on the front side. Accordingly, it is preferable that the angle of view of the front image is large.

In contrast, an irradiation-direction image is used to accurately confirm the situation of the subject H and a situation around the subject, such as a positional relationship between the subject H and the radiation detector 80. Accordingly, since it is easier to concentrate on work relating to the taking of a radiation image in a case in which there is no unnecessary peripheral information and the irradiation-direction image can also be enlarged and displayed in a case in which the angle of view is reduced, it is preferable that the angle of view of an irradiation-direction image is small. Therefore, it is preferable that the imaging angle of view of the camera for an irradiation-direction image is smaller than the imaging angle of view of the camera for a front image.

Further, it is preferable that the resolution of the camera for an irradiation-direction image is higher than the resolution of the camera for a front image. In this case, since an operator can more accurately confirm a situation around the subject H from the irradiation-direction image that is displayed on the monitor 23, the operator can more accurately perform work relating to the taking of a radiation image, such as the setting of the position of the radiation source unit 40.

Furthermore, it is preferable that the frame rate of the camera for a front image is higher than the frame rate of the camera for an irradiation-direction image. That is, since a front image is basically taken during the travel in which the radiation-irradiation device 1 is being moved, it is preferable that a front image displayed on the monitor 23 is smoother and allows the field of view on the front side in the traveling direction of the radiation-irradiation device 1 to be more easily confirmed. In contrast, since an irradiation-direction image is generally to show the field of view around the subject H without quick motion, the frame rate may be relatively low.

In regard to a frame rate and resolution, an internal set value of one camera may be made to vary according to, for example, a place in which the camera is disposed to selectively obtain the following characteristics (1) and (2) so that one camera functions like two cameras. One camera may be used while being switched to the taking of an irradiation-direction image and the taking of a front image, may be a dedicated camera for taking an irradiation-direction image, and may be dedicated camera for taking a front image.

(1) Low resolution and high frame rate
(2) High resolution and low frame rate

The characteristics (1) are to reduce resolution to prioritize a frame rate, and the characteristics (2) are to reduce a frame rate to prioritize resolution.

Further, it is preferable that the shutter speed of the camera for a front image is higher than the shutter speed of the camera for an irradiation-direction image. That is, since a front image is basically taken during the travel in which the radiation-irradiation device 1 is being moved, blur is likely to occur. Considering this problem, it is preferable that a front image displayed on the monitor 23 is taken with a higher shutter speed to suppress the occurrence of blur and to allow the field of view on the front side in the traveling direction of the radiation-irradiation device 1 to be easily confirmed. In contrast, since an irradiation-direction image is generally to show the field of view around the subject H without quick motion, a shutter speed may be relatively low. Further, in a case in which a shutter speed is set to a relatively low speed, an image, which has less noise and is easy to see, can be provided even at a dark place.

Figure 11:
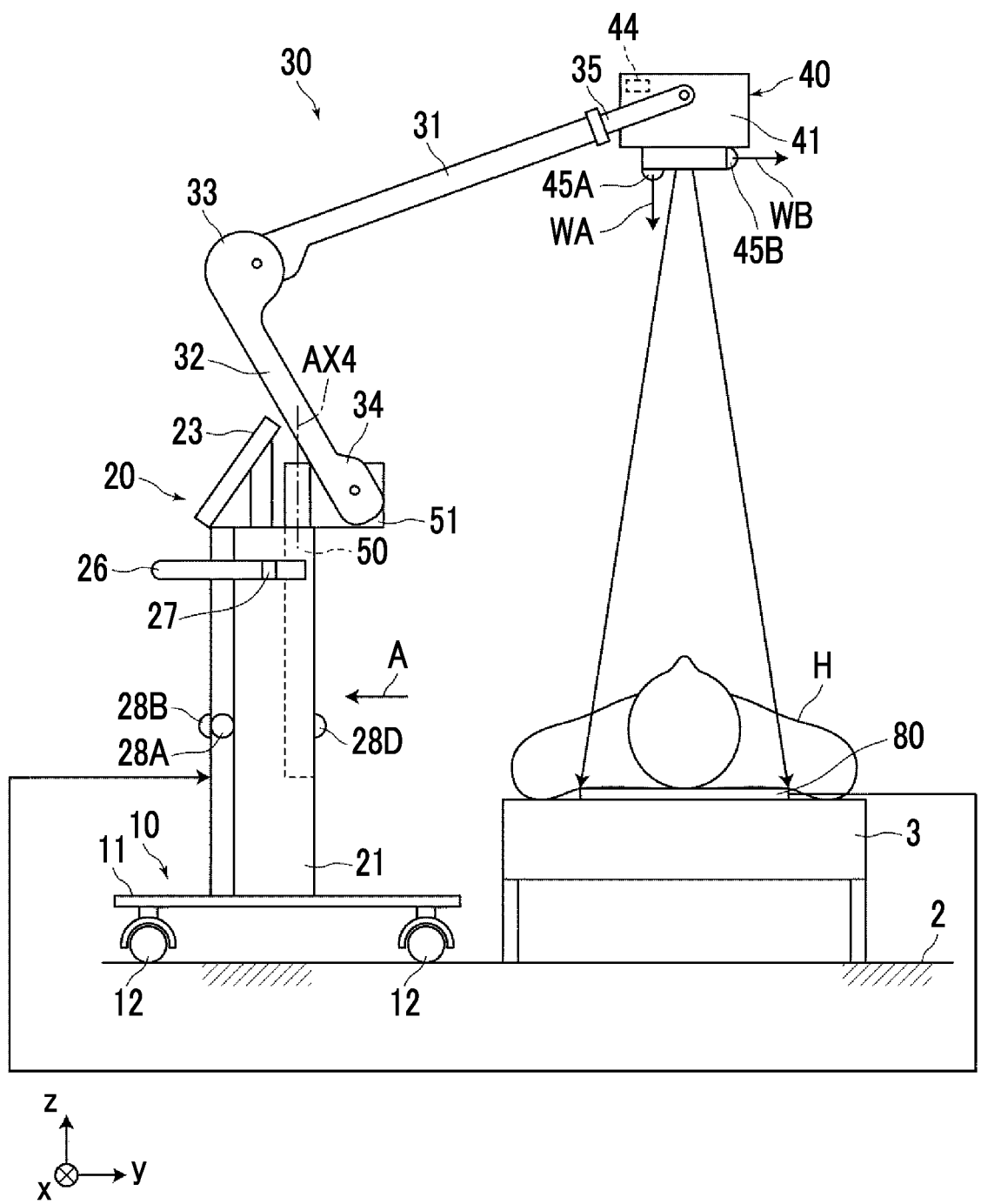
FIG. 11 is a side view of a radiation-irradiation device according to another embodiment of the invention.

In the configuration of FIG. 11, a mechanical mechanism for changing the imaging direction of the optical camera is unnecessary. Further, the two cameras 45A and 45B are required but sufficiently small cameras are provided as the cameras 45A and 45B. Accordingly, according to this configuration, the radiation source unit 40 can be formed so as to have a small size.

Next, an example of still another optical camera, which can be replaced with and used as the camera 45 of FIG. 2, will be described with reference to FIG. 13. In an example of FIG. 13, two cameras 45C and 45D are mounted on the radiation source unit 40. One camera 45C is mounted so as to face a direction in which a field of view in the radiation-irradiation direction can be imaged (the direction of an arrow WC). The other camera 45D is mounted so as to be switchable to a direction in which a field of view in the radiation-irradiation direction can be imaged (the direction of an arrow WD1) and a direction in which a field of view on the front side of the radiation-irradiation device 1 can be imaged (the direction of an arrow WD2) in a case in which the radiation source unit 40 is set to the downward direction. That is, the camera 45C takes an irradiation-direction image, and the camera 45D can take an irradiation-direction image and a front image while being switched to an irradiation-direction image and a front image. The direction of the camera 45D is switched by, for example, a publicly known actuator.

According to the above-mentioned configuration, an irradiation-direction image is taken using the two cameras 45C and 45D, which are spaced apart from each other, and a source image receptor distance (SID) and information about the thickness of the subject H can be acquired on the basis of parallax between both the cameras. Accordingly, scattered rays are estimated from these kinds of information, and a radiation image can be corrected by a so-called virtual grid so that an influence of scattered rays is removed. The virtual grid is disclosed in detail in, for example, JP2014-207958A.

Next, an example of yet another optical camera, which can be replaced with and used as the camera 45 of FIG. 2, will be described with reference to FIG. 14. In an example of FIG. 14, two cameras 45D and 45E are mounted on the radiation source unit 40. One camera 45D is the same camera as the camera used in the configuration of FIG. 13, and is mounted so as to be switchable to a direction in which a field of view in the radiation-irradiation direction can be imaged (the direction of an arrow WD1) and a direction in which a field of view on the front side of the radiation-irradiation device 1 can be imaged (the direction of an arrow WD2) in a case in which the radiation source unit 40 is set to the downward direction. The other camera 45E is mounted so as to face a direction in which a field of view on the front side of the radiation-irradiation device 1 can be imaged (the direction of an arrow WE) in a case in which the radiation source unit 40 is set to the downward direction. That is, the camera 45D can take an irradiation-direction image and a front image while being switched to an irradiation-direction image and a front image, and the camera 45E takes a front image.

According to the above-mentioned configuration, a so-called stereo camera is used as each of the two cameras 45D and 45E and can determine whether or not an object present on the front side in the transport direction of the radiation-irradiation device 1 is a three-dimensional obstacle as described above.

Next, an example of another optical camera, which can be replaced with and used as the camera 45 of FIG. 2, will be described with reference to FIG. 15. In an example of FIG. 15, two cameras 45D and 45F are mounted on the radiation source unit 40. One camera 45D is the same camera as the camera used in the configuration of FIGS. 13 and 14, and is mounted so as to be switchable to a direction in which a field of view in the radiation-irradiation direction can be imaged (the direction of an arrow WD1) and a direction in which a field of view on the front side of the radiation-irradiation device 1 can be imaged (the direction of an arrow WD2) in a case in which the radiation source unit 40 is set to the downward direction. The other camera 45F is mounted so as to be switchable to a direction in which a field of view in the radiation-irradiation direction can be imaged (the direction of an arrow WF1) and a direction in which a field of view on the front side of the radiation-irradiation device 1 can be imaged (the direction of an arrow WF2) in a case in which the radiation source unit 40 is set to the downward direction. That is, both the cameras 45D and 45F are adapted to be capable of taking an irradiation-direction image and a front image while being switched to an irradiation-direction image and a front image.

Figure 13:
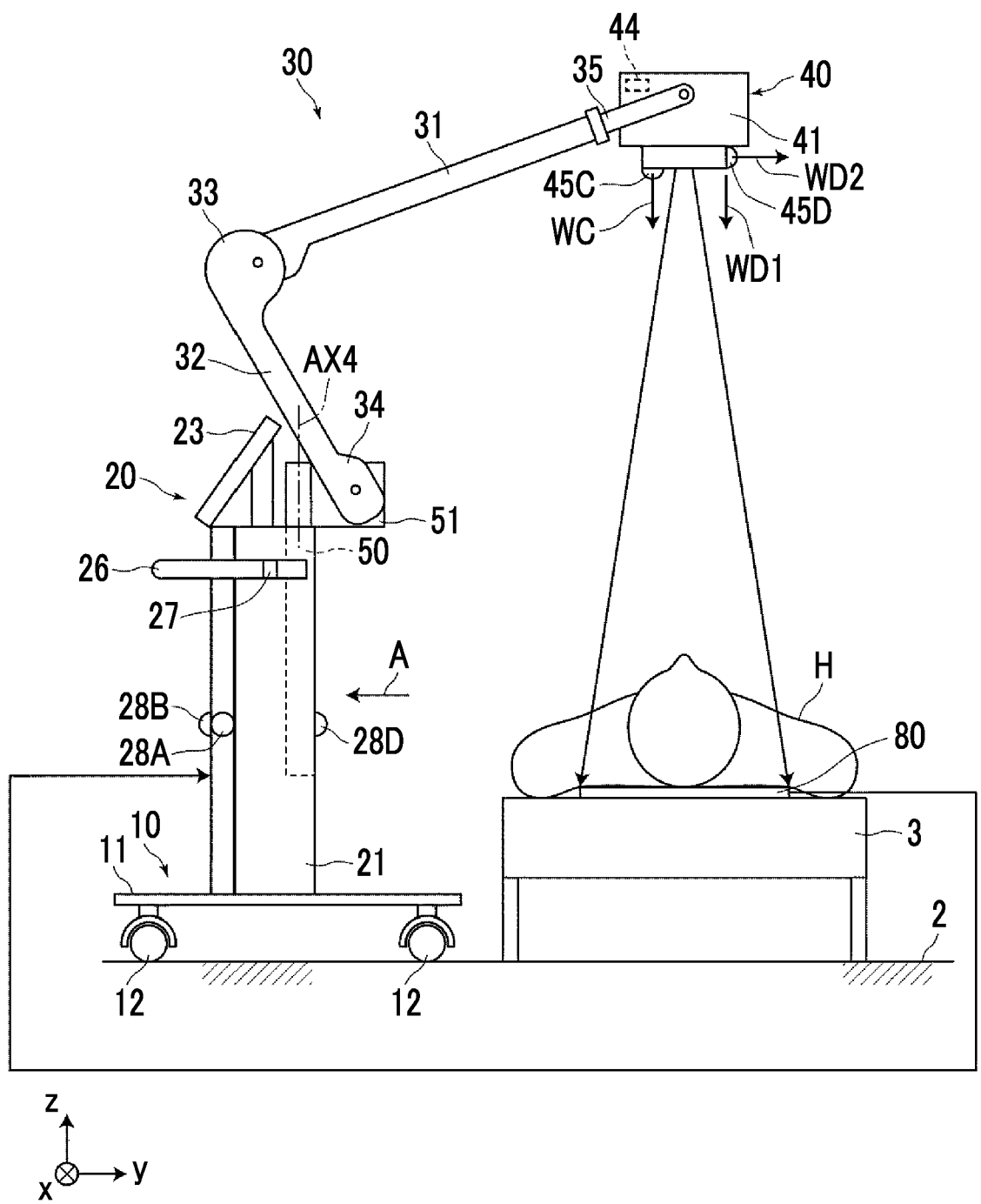
FIG. 13 is a side view of a radiation-irradiation device according to still another embodiment of the invention.
Figure 14:
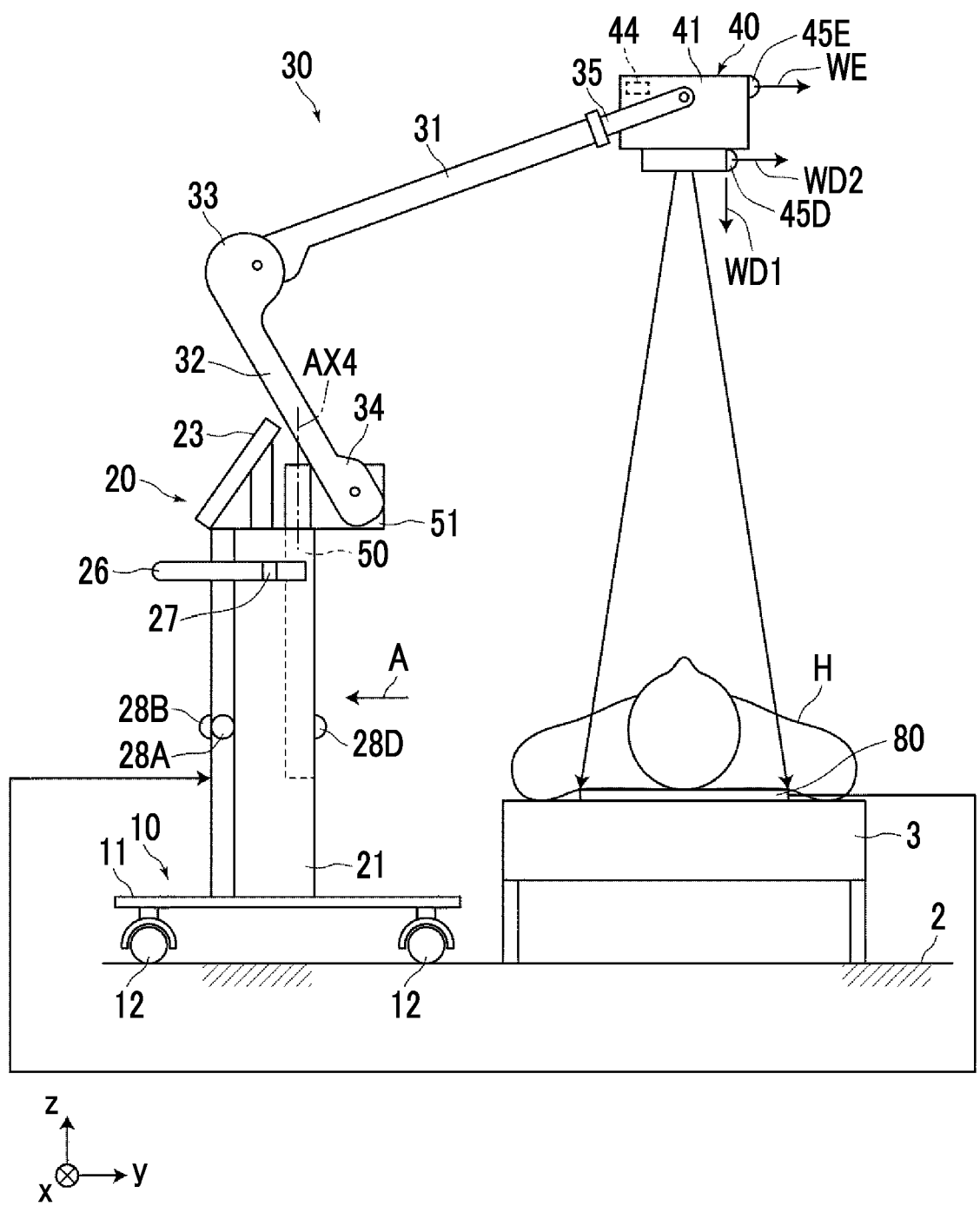
FIG. 14 is a side view of a radiation-irradiation device according to still another embodiment of the invention.
Figure 15:
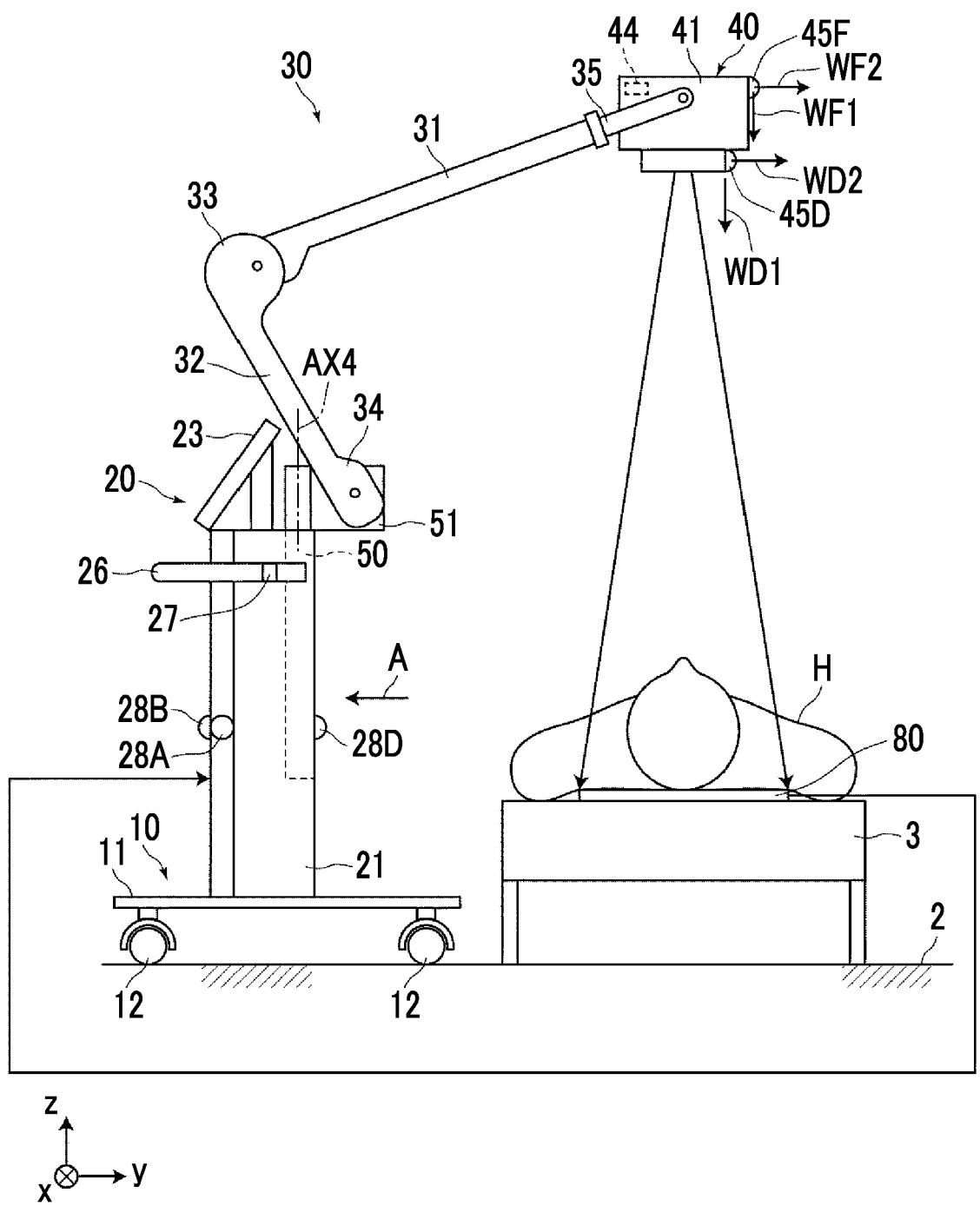
FIG. 15 is a side view of a radiation-irradiation device according to still another embodiment of the invention.

In the configuration of FIGS. 13 to 15, the cameras 45A to 45F are mounted on the radiation source units 40. However, the installation positions of these cameras 45A to 45F are not limited to the radiation source units 40. However, in a case in which the cameras 45A to 45F are mounted on the radiation source units 40, the directions of the cameras 45A to 45F can be changed according to the directions of the radiation source units 40. Accordingly, considering this, it is preferable that the cameras are mounted on the radiation source units 40.

According to the above-mentioned configuration, both the functional effect obtained from the configuration of FIG. 13 and the functional effect obtained from the configuration of FIG. 14 can be obtained.

Next, monitor image display methods for a radiation-irradiation device according to embodiments of the invention will be described with reference to flow charts of FIGS. 16 and 17. The same steps as the above-mentioned steps shown in FIG. 7 are denoted in FIGS. 16 and 17 by the same reference numerals as the reference numerals shown in FIG. 7, and the description thereof will be omitted as long as the same steps do not particularly need to be described. Further, the embodiments of which the flow charts are shown in FIGS. 16 and 17 basically use the configuration shown in FIGS. 1 to 6, and can be embodied by the change of the program that is executed by the control unit 22 of FIG. 6.

Figure 16:
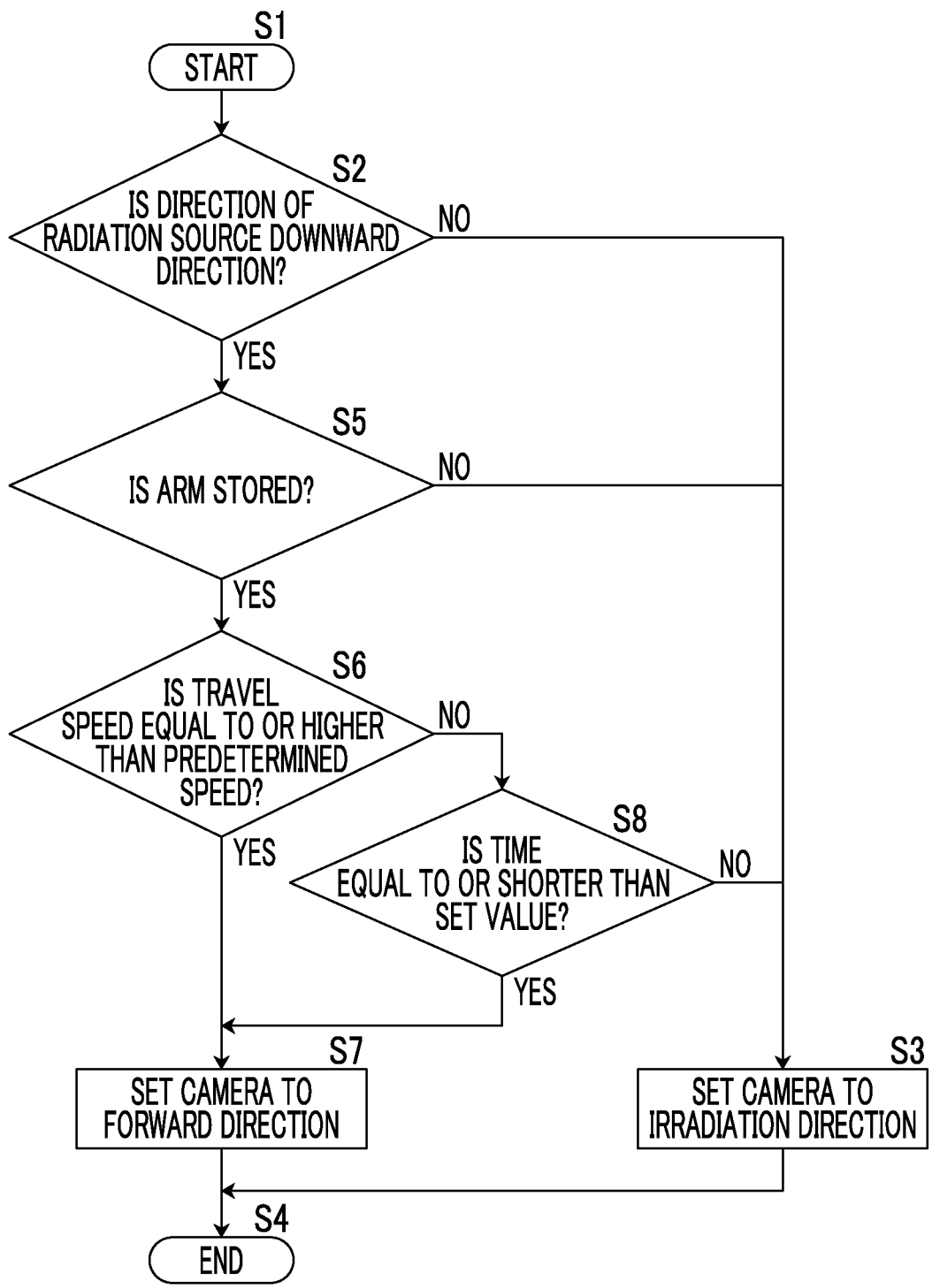
FIG. 16 is a flow chart showing the flow of a part of processing of a monitor image display method according to another embodiment of the invention.

The embodiment of which the flow chart is shown in FIG. 16 is different from the embodiment of which the flow chart is shown in FIG. 7 in that the above-mentioned four optional functions are not used at all. That is, Step S9 shown in FIG. 7 is omitted in this embodiment. If the determination of "NO" is made in Step S8, that is, if a time while the travel speed is not equal to or higher than a certain speed exceeds a set value, the control unit 22 then sets the direction of the camera 45 (see FIG. 2) to the irradiation direction in Step S3 and ends processing. The setting of the direction of the camera 45 to a forward direction in Step S7, which is performed in a case in which the determination of "YES" is made in Step S8, is the same as that of the embodiment of which the flow chart is shown in FIG. 7.

Since the determination of "NO" in Step S8 in this embodiment is thought as described above that the transport of the radiation-irradiation device 1 is stopped and the radiation-irradiation device 1 arrives at the imaging site, the direction of the camera 45 is immediately set to the irradiation direction.

Figure 17:
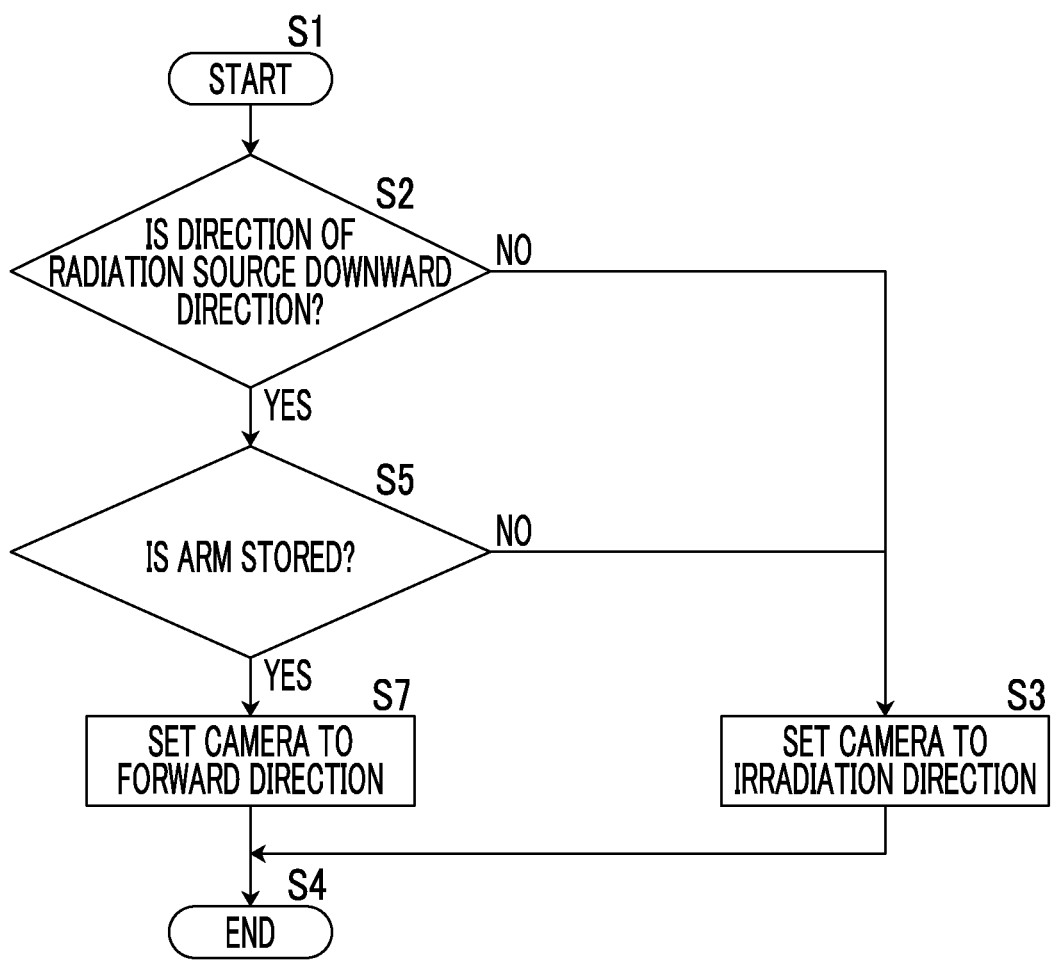
FIG. 17 is a flow chart showing the flow of a part of processing of the monitor image display method according to still another embodiment of the invention.

Next, the embodiment of which the flow chart is shown in FIG. 17 will be described. This embodiment is different from the embodiment of which the flow chart is shown in FIG. 7 in that Step S6 shown in FIG. 7 is omitted. That is, in this embodiment, if it is determined in Step S5 that the arm unit 30 (see FIG. 1) is stored, the control unit 22 then sets the direction of the camera 45 (see FIG. 2) to the forward direction in Step S7 and ends processing. The setting of the direction of the camera 45 to the irradiation direction in Step S7, which is performed in Step S3 in a case in which it is determined in Step S5 that the arm unit 30 is not stored, is the same as that of the embodiment of which the flow chart is shown in FIG. 7.

As described above in this embodiment, it is thought that the radiation-irradiation device 1 is being reliably transported if it is determined in Step S5 that the arm unit 30 is stored. Accordingly, the direction of the camera 45 is immediately set to the forward direction.

If Step S8 is not provided in the processing shown in FIG. 16 and the determination of "NO" is made in Step S6, that is, it is determined in Step S6 that the travel speed of the radiation-irradiation device 1 is lower than a preset certain speed, the direction of the camera 45 may be immediately set to the irradiation direction.

Likewise, if Step S8 is not provided in the processing shown in FIG. 7 and the determination of "NO" is made in Step S6, that is, it is determined in Step S6 that the travel speed of the radiation-irradiation device 1 is lower than a preset certain speed, processing may proceed to the processing of Step S9.

Further, if the determination of "NO" is made in Step S5 in the processing shown in FIG. 17, that is, it is determined in Step S5 that the arm unit 30 is not stored, processing may proceed to Step S9 of FIG. 7. Furthermore, if Step S5 is not provided in the processing shown in FIG. 17 and the determination of "YES" is made in Step S2, that is, it is determined in Step S2 that the radiation source unit 40 is set to the downward direction, the direction of the camera 45 may be immediately set to the forward direction.

Figure 18:
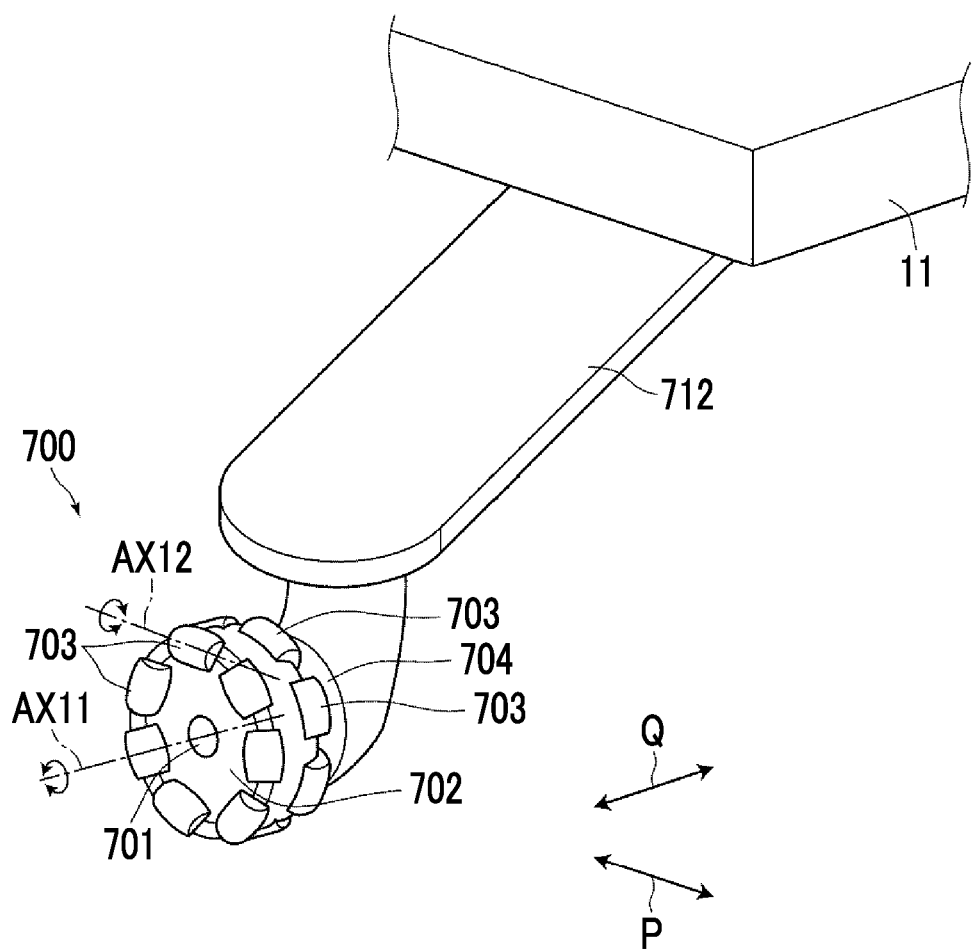
FIG. 18 is a perspective view showing another example of a wheel part that is applied to the radiation-irradiation device of the invention.

Next, in regard to a wheel part that is applied to the radiation-irradiation device 1, an example of the wheel part other than the above-mentioned caster-shaped wheel part 12 will be described here. A wheel part shown in FIG. 18 is formed of, for example, OMNI WHEEL (registered trademark). FIG. 18 shows a state in which the OMNI WHEEL 700 is mounted on the base 11 of the radiation-irradiation device 1 shown in FIG. 1 through a leg holding portion 712 as an example.

The OMNI WHEEL 700 is one of omnidirectionally moving wheels, and includes a rotating body 702 that is mounted on an axle 701 and is rotatable about a rotation axis AX11 in a normal direction and a reverse direction, and a plurality of rollers 703 that are mounted on the outer peripheral portion of the rotating body 702. For example, a barrel-shaped roller is applied as the roller 703.

In this example, seven rollers 703 are mounted on each of left and right sides of the rotating body 702, that is, a total of fourteen rollers 703 are mounted on the rotating body 702. Each of the seven rollers 703, which are mounted on one side of the left and right sides of the rotating body, is mounted on the rotating body 702 so as to be rotatable about a rotation axis AX12, which extends in a tangential direction of one circle coaxial with the rotation axis AX11, in a normal direction and a reverse direction. The same applies to the seven rollers 703 that are mounted on the other side of the left and right sides of the rotating body. Further, the seven rollers 703, which are mounted on one side of the left and right sides of the rotating body, are disposed at positions that face gaps between the seven rollers 703 that are mounted on the other side of the left and right sides of the rotating body. The OMNI WHEEL 700 having the above-mentioned structure is mounted on each leg holding portion 712 through a bearing part 704 receiving the axle 701.

In the case of the OMNI WHEEL 700, the rotating body 702 and the fourteen rollers 703 form one rotating wheel. That is, in a case in which a force acting in the direction of an arrow P of FIG. 22 is applied to the radiation-irradiation device including the leg holding portions 712, each wheel, which includes the rotating body 702 and the rollers 703, rotates about the rotation axis AX11 while the fourteen rollers 703 serve as the outer peripheral surface of each wheel. Accordingly, the movement of the leg holding portions 712, that is, the radiation-irradiation device in the direction of the arrow P is facilitated. Further, in a case in which a force acting in the direction of an arrow Q of FIG. 22 is applied to the radiation-irradiation device including the leg holding portions 712, each of the grounded rollers 703 rotates about the rotation axis AX12. Accordingly, the movement of the leg holding portions 712, that is, the radiation-irradiation device in the direction of the arrow Q is facilitated.

For example, a mecanum wheel disclosed in JP2013-081659A can also be applied as the omnidirectionally moving wheel other than the above-mentioned OMNI WHEEL 700.

The embodiments in which the direction of the optical camera is changed by automatic control have been described above, but an operator may change the direction of the optical camera by a manual operation in the monitor image display method for a radiation-irradiation device according to the invention.

Further, the radiation-irradiation device of the above-mentioned embodiment has been made to travel by an operator's force. However, the radiation-irradiation device of the invention may include a power source, such as a motor, and may be adapted to automatically travel. Alternatively, the radiation-irradiation device of the invention may be adapted to travel by an operator's force while a drive force generated from a power source assists an operator.

EXPLANATION OF REFERENCES

1: radiation-irradiation device
2: device-placement surface
3: bed
10: leg unit
11: base
12: wheel part
18: speaker
20: body unit
21: housing
22: control unit
23: monitor
24: input unit
28A to 28D: camera
30: arm unit
31: first arm
32: second arm
40: radiation source unit
44: direction sensor
45, 45A to 45F: optical camera
46: speed sensor
47: storage sensor
50: raising/lowering mechanism
80: radiation detector
84A to 84D: marker of radiation detector
90: optical image
91: processed image
700: OMNI WHEEL

What is claimed is:

1. A monitor image display method for a radiation-irradiation device that irradiates a radiation image recording medium with radiation to take a radiation image and is adapted to be capable of traveling, the radiation-irradiation device including
a radiation source that generates radiation,
a radiation source holding unit that is capable of at least setting the radiation source to a direction in which the radiation source irradiates the radiation image recording medium with radiation at the time of radiation irradiation and setting the radiation source to a vertically downward direction,
at least one optical camera that is capable of taking at least a front image showing a field of view on a front side in a traveling direction of the radiation-irradiation device and an irradiation-direction image showing a field of view in a radiation-irradiation direction at the time of radiation irradiation, and
a monitor that displays the image taken by the optical camera, the monitor image display method comprising:
displaying the irradiation-direction image on the monitor in a case in which the radiation source is set to a direction other than a downward direction;
displaying the irradiation-direction image on the monitor in a case in which the radiation source is set to the downward direction and a first condition is satisfied; and
displaying the front image on the monitor in a case in which the radiation source is set to the downward direction and a second condition different from the first condition is satisfied.

2. The monitor image display method for a radiation-irradiation device according to claim 1,
wherein in a case in which the radiation source holding unit is to take a non-storage state where the radiation source holding unit is unfolded and a storage state, a condition in which the radiation source holding unit is in the non-storage state is set as the first condition and a condition in which the radiation source holding unit is in the storage state is set as the second condition.

3. The monitor image display method for a radiation-irradiation device according to claim 1,
wherein in a case in which the radiation source holding unit is to take a non-storage state where the radiation source holding unit is unfolded for radiation irradiation and a storage state where radiation irradiation is not performed, a condition in which the radiation source holding unit is in the non-storage state is set as the first condition and a condition in which the radiation source holding unit is in the storage state and a travel speed of the radiation-irradiation device is equal to or higher than a predetermined speed is set as the second condition.

4. The monitor image display method for a radiation-irradiation device according to claim 1, further comprising:
switching an image, which is to be displayed on the monitor, to the irradiation-direction image or the front image in accordance with a travel speed of the radiation-irradiation device.

5. The monitor image display method for a radiation-irradiation device according to claim 4, further comprising:
displaying the front image on the monitor in a case in which the travel speed is equal to or higher than the predetermined speed.

6. The monitor image display method for a radiation-irradiation device according to claim 4, further comprising:
displaying the irradiation-direction image on the monitor in a case in which the travel speed is lower than the predetermined speed.

7. The monitor image display method for a radiation-irradiation device according to claim 4, further comprising:
displaying the irradiation-direction image on the monitor in a case in which a time while the travel speed is lower than the predetermined speed exceeds a predetermined time; and
displaying the front image on the monitor in a case in which a time while the travel speed is lower than the predetermined speed is equal to or shorter than the predetermined time.

8. The monitor image display method for a radiation-irradiation device according to claim 4, further comprising:
displaying the irradiation-direction image on the monitor in a case in which the travel speed is lower than the predetermined speed and a predetermined additional condition is satisfied.

9. The monitor image display method for a radiation-irradiation device according to claim 4, further comprising:
displaying the irradiation-direction image on the monitor in a case in which a time while the travel speed is lower than the predetermined speed exceeds a predetermined time and a predetermined additional condition is satisfied.

10. The monitor image display method for a radiation-irradiation device according to claim 8, wherein the additional condition is a condition in which a power source of the radiation image recording medium is turned on.

11. The monitor image display method for a radiation-irradiation device according to claim 8, wherein the additional condition is a condition in which the radiation-irradiation device detects the radiation image recording medium.

12. The monitor image display method for a radiation-irradiation device according to claim 8, wherein the additional condition is a condition in which a trigger signal for making the radiation-irradiation device be in an imaging preparation state is generated from a console of the radiation-irradiation device.

13. The monitor image display method for a radiation-irradiation device according to claim 8, wherein in a case in which an exposure switch of which a pressing operation is performed by two stages is used as an exposure switch for driving the radiation source, the additional condition is a condition in which a first-stage pressing operation of the exposure switch is performed.

14. The monitor image display method for a radiation-irradiation device according to claim 1, wherein one optical camera, of which a direction is changed to a case in which the front image is to be taken and a case in which the irradiation-direction image is to be taken, is used as the optical camera.

15. The monitor image display method for a radiation-irradiation device according to claim 1, wherein a dedicated optical camera for taking the front image and a dedicated optical camera for taking the irradiation-direction image are used as the optical camera.

16. The monitor image display method for a radiation-irradiation device according to claim 15, wherein cameras of which at least one of imaging angles of view, resolutions, frame rates, and shutter speeds are different from each other are used as the dedicated optical camera for taking the irradiation-direction image and the dedicated optical camera for taking the front image.

17. A radiation-irradiation device that irradiates a radiation image recording medium with radiation to take a radiation image and is adapted to be capable of traveling, the radiation-irradiation device comprising:
a radiation source that generates radiation;
a radiation source holding unit that is capable of at least setting the radiation source to a direction in which the radiation source irradiates the radiation image recording medium with radiation at the time of radiation irradiation and setting the radiation source to a vertically downward direction;
at least one optical camera that is capable of taking at least a front image showing a field of view on a front side in a traveling direction of the radiation-irradiation device and an irradiation-direction image showing a field of view in a radiation-irradiation direction at the time of radiation irradiation;
a monitor that displays the image taken by the optical camera;
a direction detecting unit that detects a direction of the radiation source; and
a display control unit that displays the irradiation-direction image on the monitor in a case in which the direction of the radiation source detected by the direction detecting unit is set to a direction other than the downward direction, displaying the irradiation-direction image on the monitor in a case in which the radiation source is set to the downward direction and a first condition is satisfied, and displaying the front image on the monitor in a case in which the radiation source is set to the downward direction and a second condition different from the first condition is satisfied.

18. The radiation-irradiation device according to claim 17, wherein the radiation source holding unit is to take a non-storage state where the radiation source holding unit is unfolded for radiation irradiation and a storage state where radiation irradiation is not performed, the radiation-irradiation device further comprising:
a state detecting unit that detects which of the non-storage state and the storage state the radiation source holding unit is in; and
a speed detecting unit that detects a travel speed of the radiation-irradiation device,
wherein the display control unit uses a condition, in which the state of the radiation source holding unit detected by the state detecting unit is the non-storage state, as the first condition and uses a condition, in which the state of the radiation source holding unit detected by the state detecting unit is the storage state, as the second condition.

19. The radiation-irradiation device according to claim 17, wherein the radiation source holding unit is to take a non-storage state where the radiation source holding unit is unfolded for radiation irradiation and a storage state where radiation irradiation is not performed, the radiation-irradiation device further comprising:
a state detecting unit that detects which of the non-storage state and the storage state the radiation source holding unit is in; and
a speed detecting that detects a travel speed of the radiation-irradiation device,
wherein the display control unit uses a condition, in which the state of the radiation source holding unit detected by the state detecting unit is the non-storage state, as the first condition and uses a condition, in which the state of the radiation source holding unit detected by the state detecting unit is the storage state and the travel speed detected by the speed detecting unit is equal to or higher than a predetermined speed, as the second condition.

20. The radiation-irradiation device according to claim 17, further comprising:
a speed detecting unit that detects a travel speed of the radiation-irradiation device;
wherein the display control unit switches an image, which is to be displayed on the monitor, to the irradiation-direction image or the front image in accordance with the travel speed of the radiation-irradiation device detected by the speed detecting unit.

* * * * *